US006200322B1

(12) United States Patent
Branch et al.

(10) Patent No.: US 6,200,322 B1
(45) Date of Patent: Mar. 13, 2001

(54) MINIMAL EXPOSURE POSTERIOR SPINAL INTERBODY INSTRUMENTATION AND TECHNIQUE

(75) Inventors: Charles L. Branch, Advance, NC (US); Lawrence M. Boyd, Memphis; Eddie F. Ray, III, Cordova, both of TN (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/373,835

(22) Filed: Aug. 13, 1999

(51) Int. Cl.$^7$ .............................. A61B 17/58; A61B 17/60
(52) U.S. Cl. ........................ 606/96; 606/99; 606/104
(58) Field of Search .................................. 606/61, 72, 80, 606/96, 98, 99, 104; 128/898; 623/16.11, 17.11

(56) References Cited

U.S. PATENT DOCUMENTS

| | | | |
|---|---|---|---|
| 3,128,768 | * 4/1964 | Geistauts | 606/61 |
| 3,486,505 | 12/1969 | Morrison | 128/303 |
| 3,848,601 | 11/1974 | Ma et al. | 128/305 |
| 4,545,374 | 10/1985 | Jacobson | 128/303 |
| 4,736,738 | 4/1988 | Lipovsek et al. | 128/92 V |
| 5,026,373 | 6/1991 | Ray et al. | 606/61 |
| 5,306,275 | 4/1994 | Bryan | 606/61 |
| 5,431,658 | 7/1995 | Moskovich | 606/99 |
| 5,484,437 | * 1/1996 | Michelson | 606/61 |
| 5,489,307 | 2/1996 | Kuslich et al. | 623/17 |
| 5,505,732 | * 4/1996 | Michelson | 606/61 |
| 5,772,661 | * 6/1998 | Michelson | 606/61 |
| 5,797,909 | * 8/1998 | Michelson | 606/61 |
| 5,885,300 | * 3/1999 | Tokuhashi et al. | 606/104 |
| 5,954,635 | * 9/1999 | Foley et al. | 606/69 |

FOREIGN PATENT DOCUMENTS

| | | |
|---|---|---|
| 0 796 593 A2 | 9/1997 | (EP). |
| WO 96/25103 | 8/1996 | (WO). |

OTHER PUBLICATIONS

*Surgical Technique Using Bone Dowel Instrumentation For Posterior Approach,* © 1996 Sofamor Danek (LIT.P-LIF.ST96).

*Spine,* vol. 22, No. 6, pp. 667–680 © 1997, Lippincott–Raven Publishers, entitled "Threaded Titanium Cages for Lumbar Interbody Fusions" by Charles Ray, MD., FACS, FRSH (Lond.).

* cited by examiner

*Primary Examiner*—Pedro Philogene
(74) *Attorney, Agent, or Firm*—Woodard, Emhardt, Naughton, Moriarity & McNett

(57) ABSTRACT

A surgical method for preparing a site for implantation of a spinal implant into a disc space in which the disc space is first distracted by a novel stepped distractor, followed by insertion of a novel guide sleeve including a proximal portion having an uninterrupted side wall and a distal portion having a side wall defining a longitudinal opening extending along its entire length. The guide sleeve is seated adjacent the disc space with the longitudinal opening positioned opposite the dural region of the spine to provide a working channel to the disc space. A cutting tool is then inserted through the guide sleeve to remove tissue and bone laterally extending into the interior of the guide sleeve through the longitudinal opening, but only as much as necessary for passage of the spinal implant. In a further embodiment, a protective barrier, including a pair of overlapping, flexible leaf members, is operably attached to the inside surface of the guide sleeve and positioned across the longitudinal opening to separate the inner region of the guide sleeve from the outer surgical environment.

70 Claims, 14 Drawing Sheets

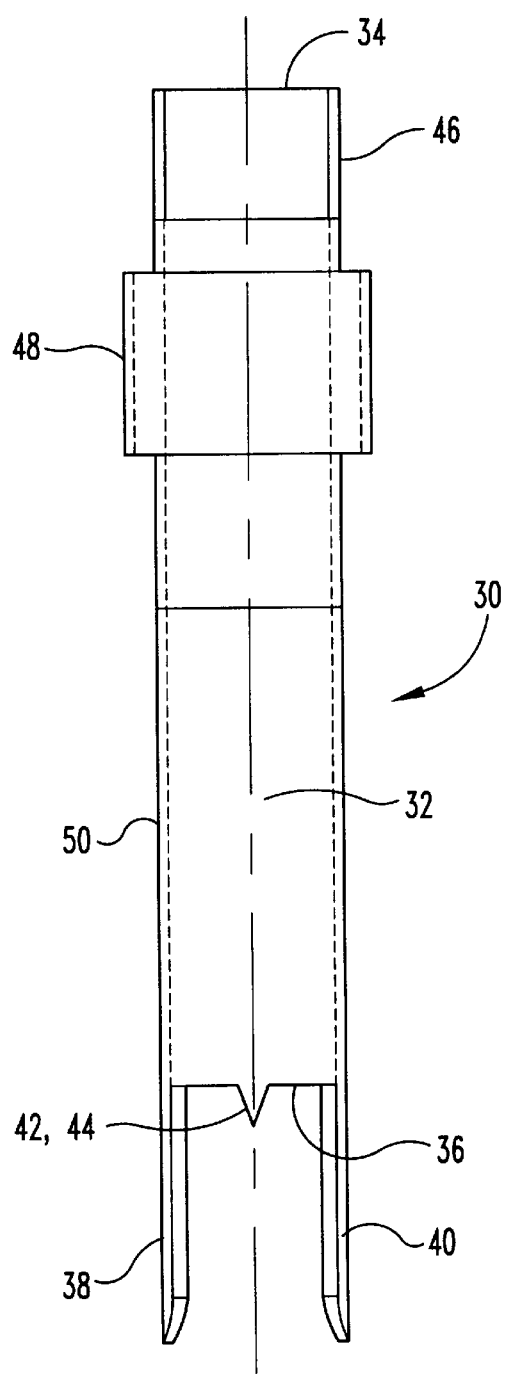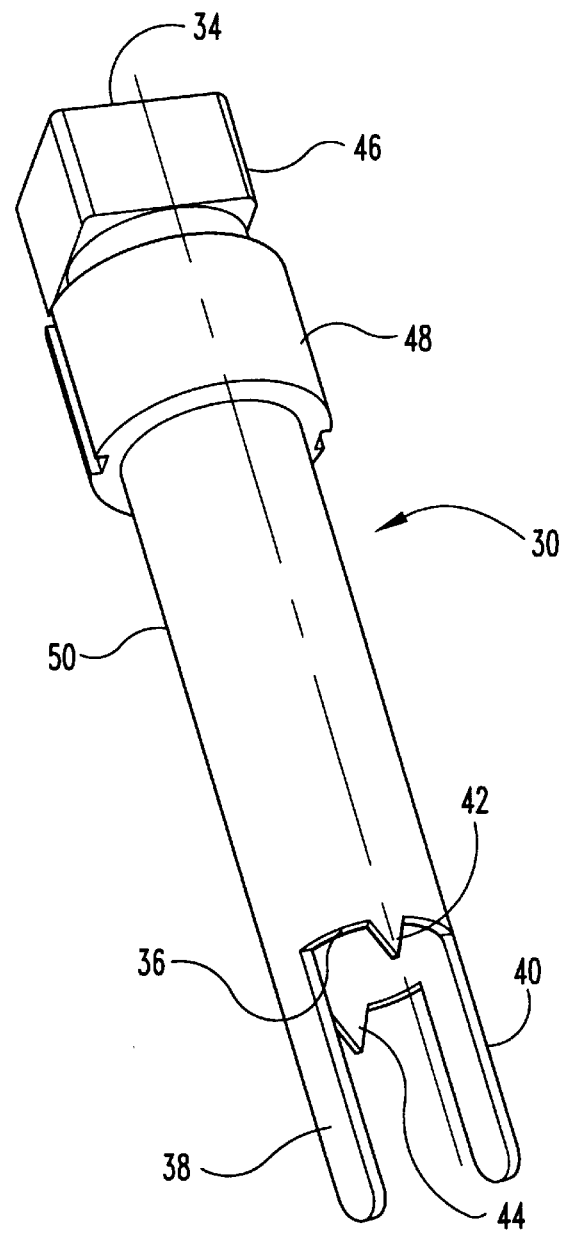
Fig. 2a
*(Prior Art)*
Fig. 2b
*(Prior Art)*

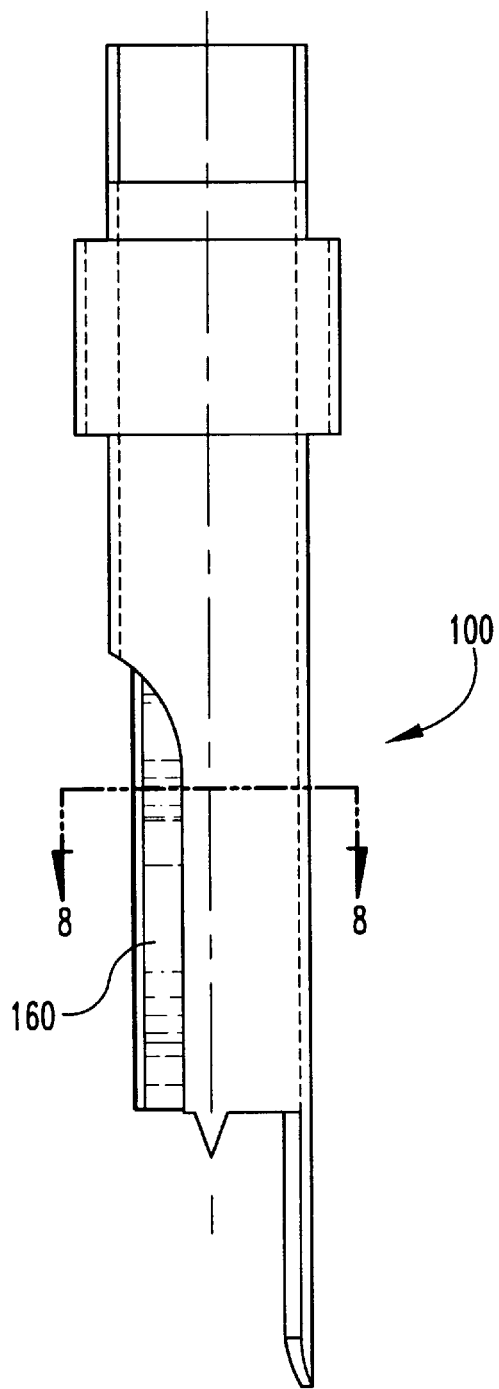
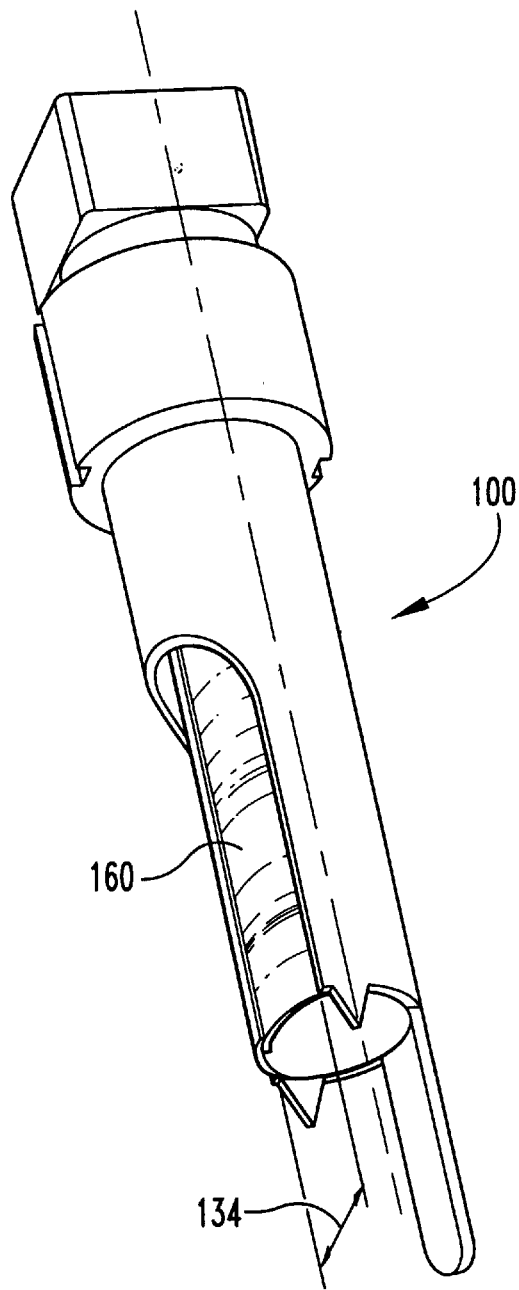
Fig.7a  Fig.7b

MINIMAL EXPOSURE POSTERIOR SPINAL INTERBODY INSTRUMENTATION AND TECHNIQUE

BACKGROUND OF THE INVENTION

The present invention relates generally to surgical spinal stabilization and more specifically to the instrumentation and technique for inserting a spinal implant within the intervertebral disc space between adjacent vertabra. More particularly, one embodiment of the present invention includes a protective guide sleeve used in conjunction with posterior spinal implant surgery for protecting neural structures and guiding associated surgical instrumentation.

Chronic back problems cause pain and disability for a large segment of the population. The number of spinal surgeries to correct causes of back pain have steadily increased over the past several years. Most often, back pain originates from damage or defects in the spinal disks between adjacent vertebrae. The disk can be herniated or can be suffering from a variety of degenerative conditions, so that in either case, the anatomical function of the spinal disk is disrupted. The most prevalent surgical treatment for these types of conditions has been to fuse the two adjacent vertebrae surrounding the affected disk. In most cases, the entire disk will be removed except for the annulus by way of a discectomy procedure. Since the damaged disk material has been removed, something must be positioned within the intradiscal space to prevent the collapse of the space which results in damage to the nerves extending along the spinal column. The intradiscal space is often filled with bone or a bone substitute in order to prevent disk space collapse and to further promote fusion of the two adjacent vertebrae.

There have been an extensive number of attempts made to develop an acceptable intradiscal implant that could be used to replace a damaged disk and maintain the stability of the disk space between adjacent vertebrae, at least until complete arthrodesis is achieved. These interbody fusion devices have taken many forms. For example, one of the more prevalent designs takes the form of a cylindrical implant. These types of implants are represented by patents to Bagby, U.S. Pat. No. 4,501,269; Brantigan, U.S. Pat. No. 4,878,915; Ray, U.S. Pat. Nos. 4,961,740 and 5,055,104; and Michelson, U.S. Pat. No. 5,015,247. In these cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intradiscal space and the vertebral end plates. These types of devices are represented by the patents to Brantigan, U.S. Pat. Nos. 4,743,256, 4,834,757 and 5,192,327.

Various surgical methods have been devised for the implantation of fusion devices into the intradiscal space. Both anterior and posterior surgical approaches have been used for interbody fusions. In 1956, Ralph Cloward developed a method and instrumentation for anterior spinal interbody fusion of the cervical spine. Cloward surgically removed the disk material and placed a tubular drill guide with a large foot plate and prongs over an aligner rod and then embedded the prongs into adjacent vertebrae. The drill guide served to maintain the alignment of the vertebrae and facilitated the reaming out of bone material adjacent the disk space. The reaming process created a bore to accommodate a bone dowel implant. The drill guide was thereafter removed following the reaming process to allow for the passage of the bone dowel which had an outer diameter significantly larger than the reamed bore and the inner diameter of the drill guide. The removal of the drill guide left the dowel insertion phase completely unprotected. Thus, Cloward's method and instrumentation was designed for and limited to an anterior surgical approach and was inappropriate for a posterior application.

Furthermore, B. R. Wilterberger described in a paper entitled "Dowel Intervertebral Fusion as Used in Lumbar Disc Surgery" (published in *The Journal of Bone and Joint Surgery*, volume 39A, pgs. 234–92, 1957), the unprotected drilling of a hole from the posterior into the lumbar spine between the nerve roots and across the disk space, and then inserting a bone dowel into that disk space. While Wilterberger had taken the Cloward concept of circular drilling and dowel fusion and applied it to the lumbar spine from a posterior approach, he had not provided for an improved method, nor had he advanced the instrumentation so as to make that procedure significantly safe. Therefore, the Wilterberger procedure rapidly feel into disrepute.

Thereafter, a patent to Michelson, U.S. Pat. No. 5,484,437 disclosed a technique and associated instrumentation for inserting a fusion device from a posterior surgical approach. As described in more detail in the '437 patent, the surgical technique involves the use of a distractor having a penetrating portion that urges the vertebral bodies apart to facilitate the introduction of the necessary surgical instrumentation. The long distractor can act as a guide for drilling and reaming tools concentrically advanced over the outside of the distractor to prepare the site for the insertion of the fusion device. The '437 patent also discloses a hollow sleeve having teeth at one end that are driven into the vertebrae adjacent the disk space created by the distractor. These teeth maintain the disk space height during subsequent steps of the procedure following removal of the distractor. In accordance with one aspect of the Michelson invention, a drill is passed through the hollow sleeve to remove portions of the disk material and vertebral bone to produce a prepared bore for insertion of the fusion device. The drill is then removed from the sleeve and the fusion device is positioned within the disk space using an insertion tool.

While the Michelson technique and instrumentation represent a significant advance over prior surgical procedures for the preparation of the disk space and insertion of the fusion device, it has limitations. One such limitation is that the Michelson technique and instrumentation requires extensive removal of lamina and facet bony structures prior to commencement of the procedure to allow for the hollow sleeve to be positioned adjacent the fusion site. Because the facet joint generally adds stability to the spinal posterior column in a variety of loading modes, generally resisting sheer, torsion and flexion loads via its configuration in combination with the capsular ligaments, it would be beneficial to limit facet and lamina removal to the exact amount required for implant insertion While a greater amount of lateral facet removal generally requires less medial retraction of the dura to allow for the unimpeded insertion of the protective guide sleeve, this increased removal of bony structure decreases the overall stability of the spine. Alternately, if a smaller implant is used to thereby reduce the amount of vertebral bone removal, the result will be lesser intradiscal distraction and reduced tensioning of the annulus. Furthermore, a smaller surface area of engagement between the implant and the adjacent vertebrae will result in reduced stability and a decreased likelihood of interbody fusion over this reduced decorticated surface.

Thus, procedures and instruments that preserve the integrity of the surgical site, and more specifically, the spinal posterior column, are desirable. Although the prior techniques and instrumentation are steps in the right direction to accurately prepare a fusion site for insertion of a spinal implant, the need for improvement still remains. The present invention is directed to this need in the field and fulfills the need in a novel and unobvious way.

SUMMARY OF THE INVENTION

The present invention relates to instrumentation and techniques for spinal interbody fusion using a minimal exposure posterior surgical approach. In one form of the present invention, a method for preparing a surgical site for implantation of a spinal implant into a disc space contemplates inserting a spinal distractor into the disc space to spread apart the upper and lower vertebra to a predetermined spacing and then positioning a guide sleeve including a proximal portion having an uninterrupted side wall and a distal portion having a side wall defining a laterally positioned longitudinal opening extending along its entire length over the spinal distractor. The guide sleeve is seated adjacent the disc space with the longitudinal opening positioned opposite the dural region of the spine to provide a working channel to the disc space. A cutting tool is then inserted through the guide sleeve to remove tissue and vertebral bone laterally extending into the interior of the guide sleeve through the longitudinal opening. The proximal portion of the guide sleeve body is generally cylindrical and defines a longitudinal passage having a generally circular transverse cross sectional area. The distal portion of the guide sleeve body is partially cylindrical and defines a longitudinal passage having a partially cylindrical transverse cross sectional area which is less than that of the cross sectional area of the proximal portion. Correspondingly, the longitudinal passage of the distal portion has a maximum width which is less than the inner diameter of the longitudinal passage of the proximal portion.

In a preferred embodiment, a cutting tool is inserted through the guide sleeve to further prepare the surgical site for insertion of the spinal implant. Cutting tools according to the present invention may be rotary cutting tools, and more specifically, cylindrical trephines. The uninterrupted side wall of the proximal portion has an inner diameter sized to receive and guide the cutting tool and other surgical instrumentation along the longitudinal axis of the guide sleeve. When the cutting tool is inserted through the guide sleeve, the cutting head of the cutting tool is capable of simultaneously removing tissue and vertebral bone, including facet material, from the adjacent vertebrae defining the disc space. Thus, the guide sleeve of the present invention provides an inner guiding surface defined by the circumferentially uninterrupted side wall of the proximal portion and also provides a protective surface defined by the partial side wall of the distal portion for protecting tissue and delicate neurological structures located generally medial and superior/inferior the longitudinal opening. Although the longitudinal opening can extend across a range of about 30 degrees to 180 degrees of the overall circumference of the distal portion, the preferred embodiment has the longitudinal opening extending across about 90 degrees of the overall circumference.

Although various sleeves are known in the art, in a preferred embodiment, the guide sleeve of the present invention includes an elongated flange projecting from its distal end having a width approximately equal to the predetermined spacing provided by the spinal distractor. The elongated flange is positioned generally opposite the longitudinal opening and is slidably received within the disc space during seating of the guide sleeve to maintain the predetermined spacing between the adjacent vertebrae. Additionally, the guide sleeve may include at least two engagement members projecting from its distal end for securing the guide sleeve in position relative to the disc space by anchoring at least one of the engagement members into each of the adjacent vertebrae. In a preferred embodiment, the engagement members are spiked protrusions.

Another form of the present invention contemplates a protective barrier positioned across the longitudinal lateral opening to separate the interior region of the guide sleeve from the outer environment. In a preferred embodiment, the protective barrier includes a pair of overlapping, flexible leaf members operably attached to the inside surface of the guide sleeve. Preferably, the protective barrier is relatively thin to allow for a certain degree of flexation and is fabricated from a metallic material such as surgical stainless steel.

In further steps of the preferred inventive technique, the spinal distractor is extracted from the disc space prior to the trephining process. Following the trephining process, a boring tool is inserted through the guide sleeve to form an implant bore within the disc space. In a preferred embodiment, the boring tool is a reamer. Following removal of the boring tool, the fusion implant is inserted through the guide sleeve and is implanted in the implant bore by way of an implant holder. If the implant is threaded, the preferred inventive technique may further include inserting a tapping tool through the guide sleeve to tap a female thread within the implant bore to prepare the bore for threaded engagement with the implant. Finally, the guide sleeve is removed from the surgical site. The preferred inventive technique can then be repeated on the other side of the disc to provide bilateral placement of two implants into a subject disc space. It is understood that the terms "dowel" and "implant" are used in a general sense and are intended to encompass dowels and implants made of bone, metallic cages and other devices used for interbody fusion regardless of shape or material of construction.

An object of the present invention is to provide surgical technique and instrumentation to promote the safe and efficient preparation of a disc space for insertion of a fusion implant from a posterior approach with minimal removal of tissue and/or vertebral bone from the surgical site. A related object is to permit the use of larger implants for interbody fusion without unduly compromising the stability of the spinal posterior column.

Other objects and benefits of the present invention can be discerned from the following written description and accompanying figures.

BRIEF DESCRIPTION OF THE DRAWINGS

FIG. 2a is a side elevational view of a protective guide sleeve used in conjunction with current posterior approach techniques.

FIG. 2b is a side perspective view of the protective guide sleeve of FIG. 2a.

FIG. 3a is a side elevational view of a distractor according to one aspect of the present invention.

FIG. 3b is a side perspective view of the distractor of FIG. 3a.

FIG. 4b is a side perspective view of the protective guide sleeve of FIG. 4a.

FIG. 5 is a sectional view taken along line 5—5 of FIG. 4a.

FIG. 6a is a sectional view taken along line 6—6 of FIG. 4a.

FIG. 7a is a side elevational view of an assembly in accordance with a further embodiment of the present invention, utilizing the protective guide sleeve of FIGS. 4a and 4b in combination with a protective barrier positioned across the longitudinal opening.

FIG. 7b is a side perspective view of the assembly of FIG. 7a.

FIG. 10b is a side perspective view of the trephine of FIG. 10a.

DESCRIPTION OF THE PREFERRED EMBODIMENT

Figure 1:
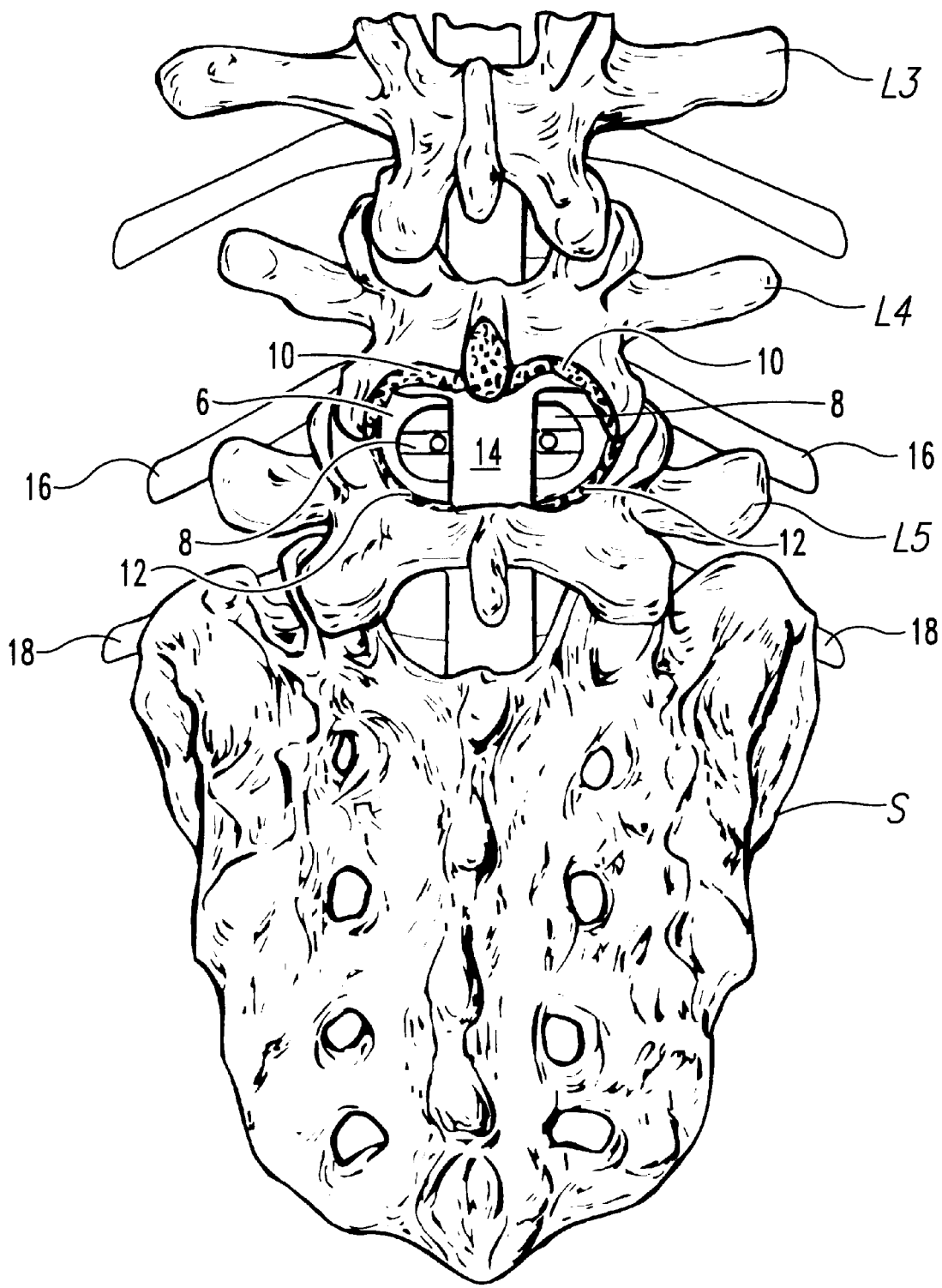
FIG. 1 is a perspective view of the posterior lumbar region of the spinal column demonstrating that the current posterior approach techniques generally involve extensive removal of lamina and facet bony structures, and also illustrating the neural structures requiring protection during a posterior surgical approach.

For the purposes of promoting an understanding of the principles of the invention, reference will now be made to the embodiments illustrated in the drawings and specific language will be used to describe the same. It will nevertheless be understood that no limitation of the scope of the invention is hereby intended, and any alterations and further modifications in the illustrated device, and any further applications of the principles of the invention as illustrated therein being contemplated as would normally occur to one skilled in the art to which the invention relates.

Referring now to FIG. 1, there is shown a portion of the lumbar region of the spinal column including an upper vertebra L4 and a lower vertebra L5 separated by a disc space 6. Shown implanted within disc space 6 are a pair of bone dowels 8. While the terms "dowel" and "implant" are repeatedly used throughout this disclosure, they are used in a general sense and are intended to encompass dowels and implants made of bone, metallic cages and other synthetic devices used for interbody fusion regardless of shape or material construction. Also shown are vertebra L3 and the sacrum S. While specific reference is made to the implantation of bone dowels within the disc space between the L4 and L5 vertebra, it will be appreciated that the present invention can be used to implant bone dowels within the disc space between the L5 vertebra and the sacrum or between any adjacent vertebrae in the spinal column.

FIG. 1 demonstrates that current posterior approach techniques and instrumentation generally involve extensive removal of lamina and facet bony structures. As is clearly illustrated, a relatively large amount of bone material must be removed from upper vertebra L4 and lower vertebra L5 to accommodate for the implantation of bone dowels 8. An inferior portion 10 of the inferior facet is symmetrically removed from both sides of upper vertebra L4. Similarly, a superior portion 12 of the superior facet is symmetrically removed from both sides of lower vertebra L5. This removal procedure provides working access to disc space 6 and a sufficiently large cavity for insertion of bone dowels 8. However, as discussed above, the removal of vertebral bone can have an adverse affect on the stability of the spinal posterior column. It is therefore an object of the present invention to limit removal of vertebral bone to the exact amount required for bone dowel implantation.

FIG. 1 also illustrates the primary neural structures requiring protection during a posterior surgical procedure. These structures include the dura 14, upper nerve roots 16 (exiting) and lower nerve roots 18 (traversing). Important to the present invention, we have noted that all of the neural structures requiring protection are either medial, superior or inferior to the implantation area. Importantly, no significant neural structures are located directly lateral the implantation area. Hence, a "safe zone" is present in this lateral region and does not require a great degree of protection during a posterior surgical approach.

Referring now to FIGS. 2a and 2b, there is shown a guide sleeve design used in conjunction with a current posterior approach technique. Sleeve 30 has an open inner cannula 32 extending from its proximal end 34 to its distal end 36. Sleeve 30 provides a working channel through which surgical instruments and spinal implants may be passed without encountering or damaging surrounding bodily tissue. Distal end 36 includes a pair of oppositely positioned distraction extensions 38 and 40. Distraction extensions 38, 40 are sized according to the height of a particular disc space and are intended to maintain the spacing between adjacent vertebra during various stages of an interbody fusion procedure. Sleeve 30 can also include oppositely positioned spiked protrusions 42, 44 disposed between distraction extensions 38, 40 to penetrate into adjacent vertebral bodies to help maintain the position of sleeve 30 relative to the surgical site. Proximal end 34 is provided with a head portion 46 configured to accept a driving cap (not shown). Sleeve 30 is seated within the surgical site by striking the driving cap with a surgical mallet (not shown) and driving distraction extensions 38, 40 into the disc space and anchoring spikes 42, 44 into the adjacent vertebrae. Sleeve 30 is also equipped with a raised knurled portion 48 to allow the surgeon to securely grip and more easily manipulate sleeve 30 within and around the surgical site, the importance of which will become apparent below. Sleeve 30 has a continuous, uninterrupted side wall 50 extending from proximal end 34 to distal end 36. Consequently, the adjacent vertebrae must be prepared to accept passage of the fill outer diameter of side wall 50. Thus, a significant amount of bony facet material must typically be removed from the upper and lower vertebrae prior to insertion of sleeve 30 within the surgical site.

Figures 3A, 3B:
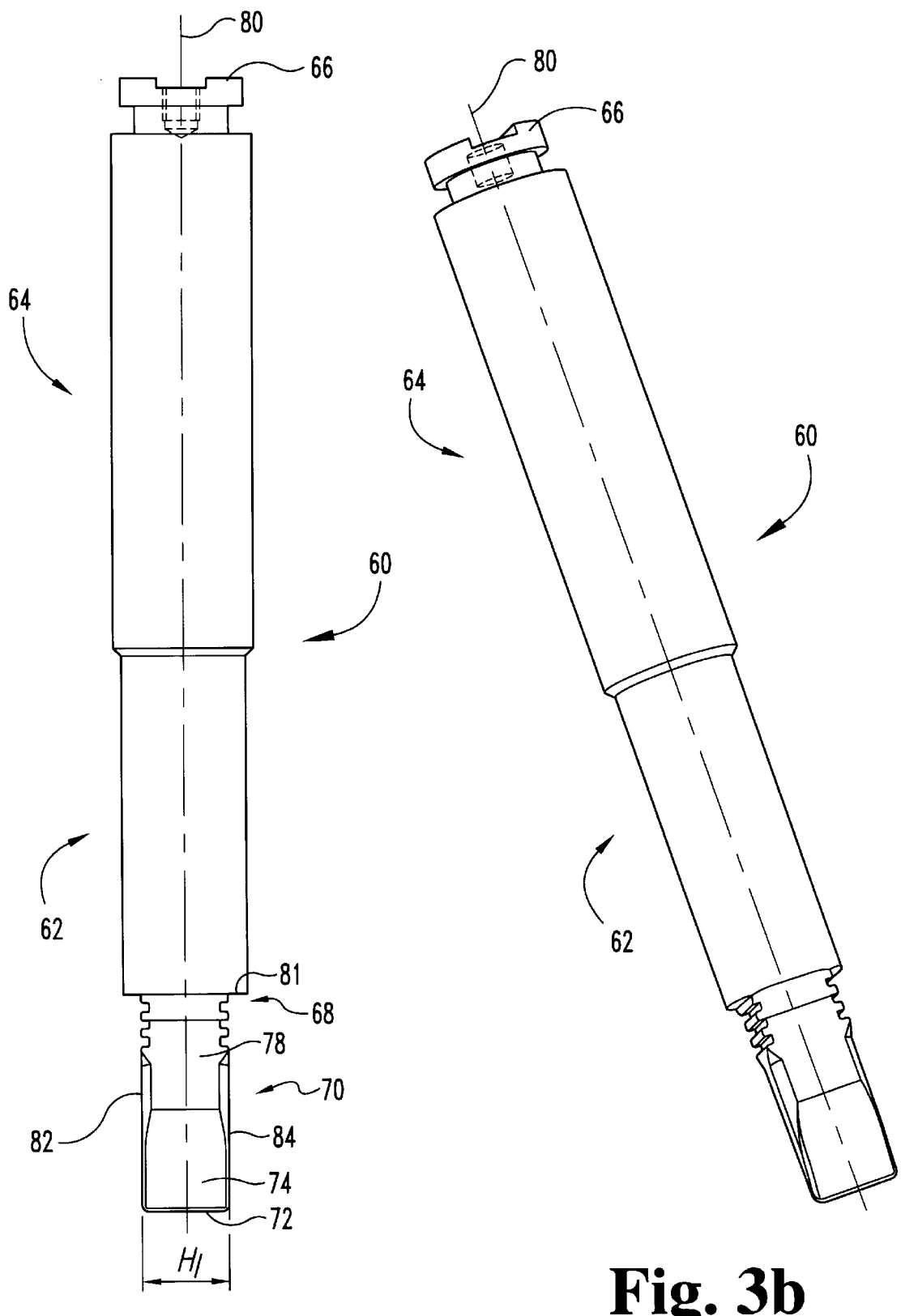

Referring now to FIGS. 3a and 3b, there is shown a spinal distractor 60 according to one aspect of the present invention. Spinal distractor 60 includes a leading portion 62 and a trailing portion 64. Leading portion 62 and trailing portion 64 preferably have a generally circular outer cross-section with leading portion 62 having a reduced cross section relative to trailing portion 64, the importance of which will become apparent below. Spinal distractor 60 includes a proximal end 66 configured for engagement with a bone dowel holder (not shown) to be described in greater detail below. In another embodiment, proximal end 66 can be configured for engagement with a conventional Hudson connection on a T-handle (not shown). The distal end 68 of leading portion 62 is joined with a distractor tip 70 that is selected according to the vertebral level being prepared for interbody fusion. Distractor tip 70 is configured such that it can be inserted into a disc space to provide a predetermined spacing between two adjacent vertebrae. More specifically, distractor tip 70 has a rounded leading edge 72 which angularly extends into inclined surface 74 and opposite inclined surface 76 (not shown). Inclined surfaces 74, 76 proximally blend into substantially planar surfaces 78 and 79 (not shown), extending in parallel alignment relative to longitudinal axis 80 of spinal distractor 60. When spinal distractor 60 is inserted into the disc space, inclined surfaces 74, 76 cooperate to distract the disc space to a first predetermined spacing. Distal end 68 of leading portion 62 also includes a circumferential shoulder 81 which is sized too large to fit within the disc space. Thus, shoulder 81 guards against the danger of overpenetration of distractor tip 70 beyond the disc space, which could possibly result in paraplegia or a life-threatening perforation of the aorta, vena cava, or iliac vessels. Once distractor tip 70 has been fully inserted to the proper depth within the disc space, spinal distractor 60 may then be rotated 90° in either direction to provide a second predetermined spacing equal to height $H_1$ of distractor tip 70. During rotation, rounded surfaces 82, 84 engage the upper and lower surfaces of adjacent vertebral bodies and urge them apart into a final disc space distraction height equal to height $H_1$. After distractor tip 70 is fully seated within the disc space, spinal distractor 60 is disengaged from the bone dowel holder (not shown) and the bone dowel holder is thereafter removed. While distractor tip 70 has been shown and described with specific structural and geometric characteristics, it is understood that various distractor tip configurations can be used to achieve the desired result of providing a final disc space distraction height $H_1$.

Figure 4A:
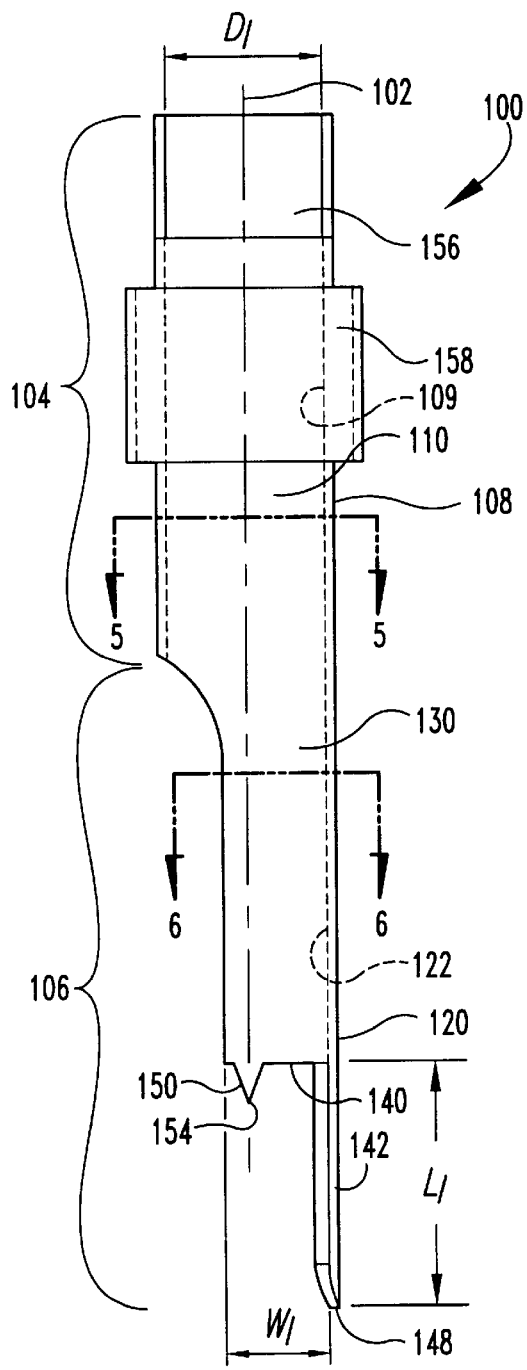
FIG. 4a is a side elevational view of a protective guide sleeve according to one aspect of the present invention.
Figure 4B:
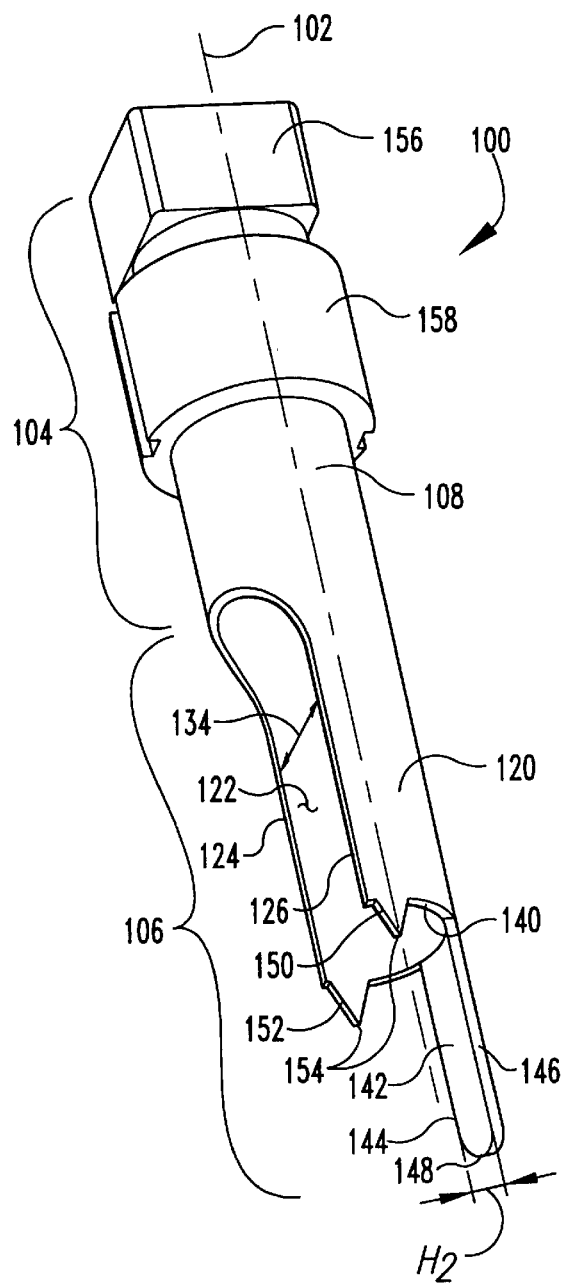
Figure 5:
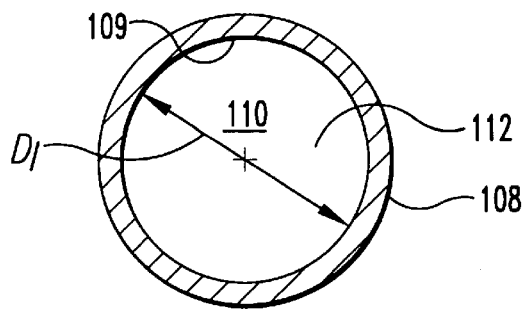
Figure 17:
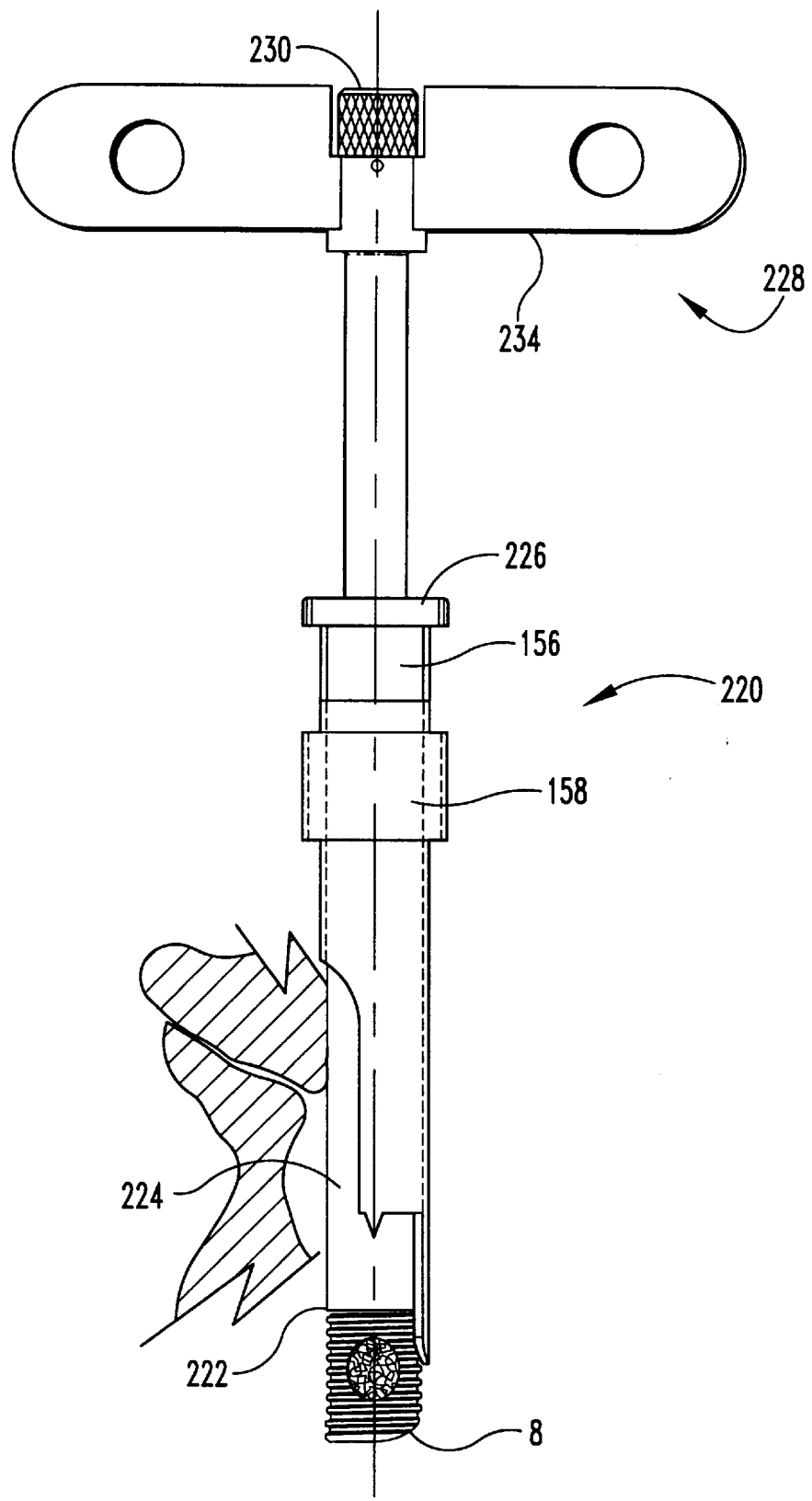
FIG. 17 is a side elevational view of a bone dowel holder positioned within the protective guide sleeve of FIGS. 4a and 4b.
Figure 18:
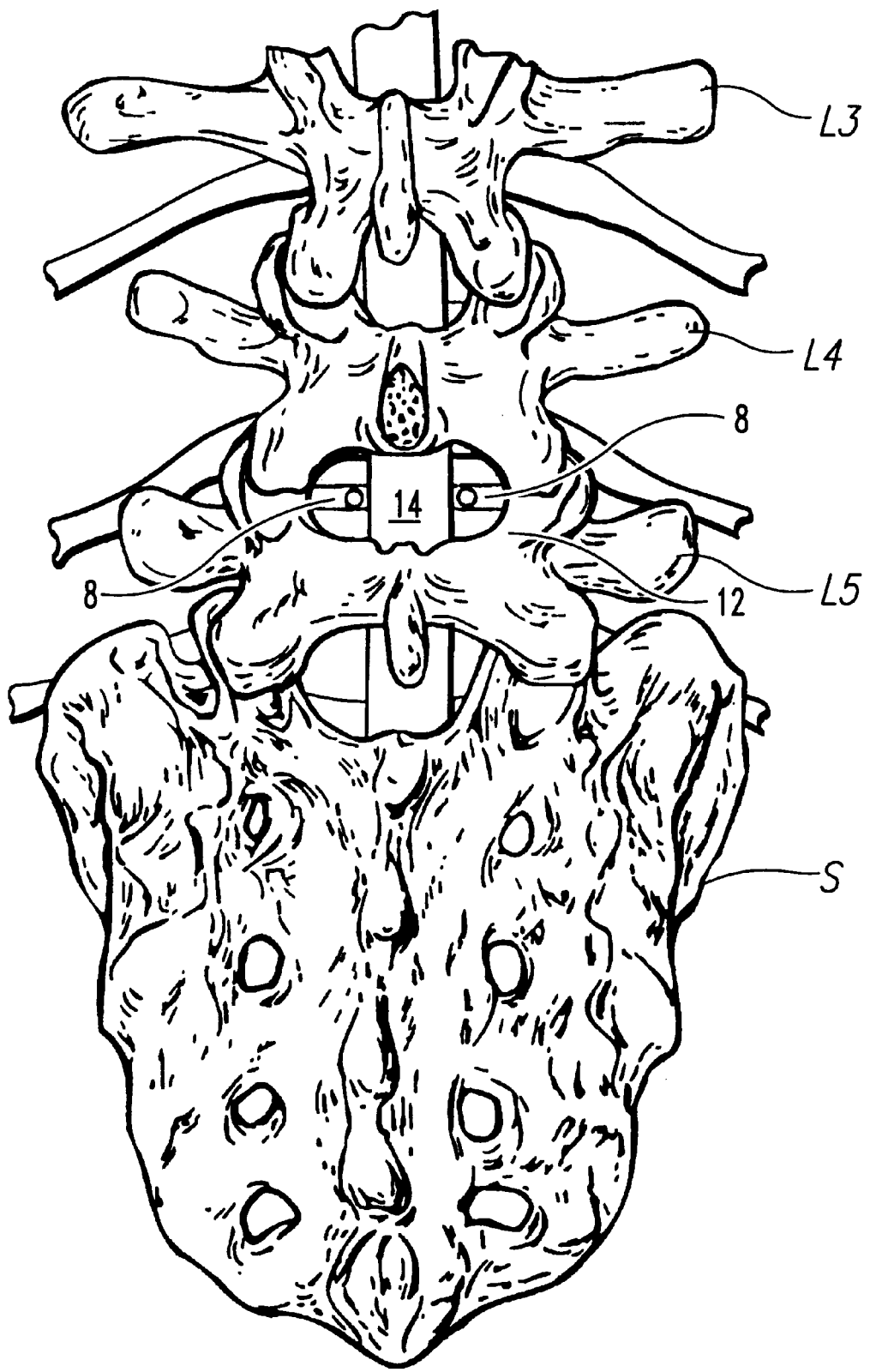
FIG. 18 is a perspective view of the posterior lumbar region of the spinal column, demonstrating that the posterior spinal interbody instrumentation and technique of the present invention requires minimal removal of vertebral bony structures in order to accommodate insertion of bone dowels into the disc space.

Referring now to FIGS. 4a and 4b, there is shown a guide sleeve 100 according to one embodiment of the present invention. Guide sleeve 100 is preferably made from metal and has a body defining a longitudinal axis 102. The body of guide sleeve 100 includes a proximal portion 104 and a distal portion 106. Proximal portion 104 includes a continuous, uninterrupted side wall 108 having an inner surface 109 forming a first longitudinal passage 110 extending along longitudinal axis 102. First longitudinal passage 110 has an inner diameter $D_1$, preferably sized slightly larger but in close tolerance to the outer diameter of bone dowel 8 (FIGS. 1, 17 and 18). Referring to FIG. 5, there is shown a sectional view taken along line 5—5 of FIG. 4a, illustrating the transverse cross-sectional area 112 of first longitudinal passage 110. While FIGS. 4a, 4b and 5 illustrate transverse cross-sectional area 112 as being generally circular, other geometric shapes are also contemplated. For instance, transverse cross-sectional area 112 could take the form of a square, triangle, hexagon, or any other suitable geometric configuration. Side wall 108 is generally cylindrical and inner surface 109 defines an inner diameter sized to accommodate and guide surgical tools and instrumentation (not shown). Thus, inner surface 109 provides a continuous, circumferentially uninterrupted inner guiding surface to guide surgical tools and instrumentation in close running fit along longitudinal axis 102 of guide sleeve 100. For purposes of the present invention, the terms "continuous" and "uninterrupted" are defined to mean that side wall 108 of proximal portion 104 does not include a longitudinal opening extending along its length. However, it should be understood that these terms do not necessarily mean that side wall 108 does not include apertures or other openings defined therein. These terms simply mean that proximal portion 104 does not include a longitudinal opening like that of longitudinal opening 134 of distal portion 106.

Figure 6A:
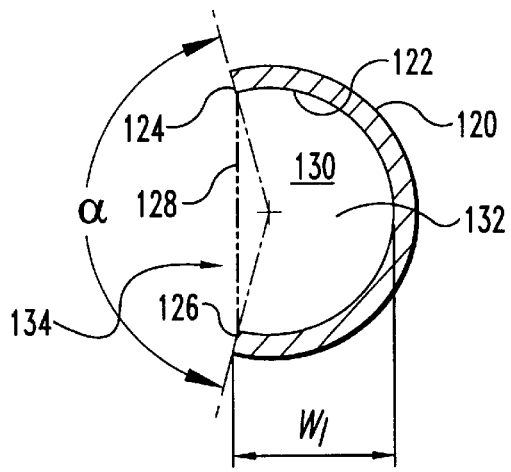
Figure 6B:
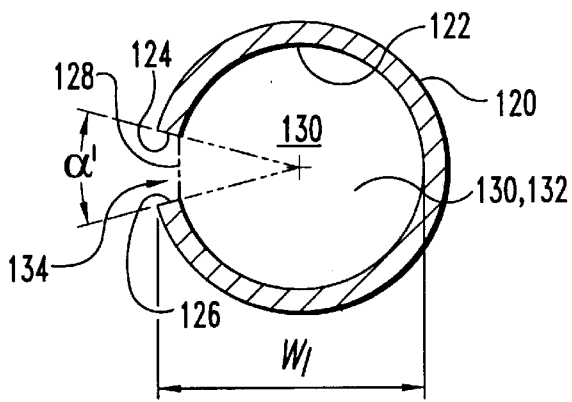
FIG. 6b is a sectional view taken at the location of line 6—6 in FIG. 4a but illustrating an alternate embodiment of the protective guide sleeve.

Distal portion 106 of guide sleeve 100 includes a side wall 120 having an inner surface 122 radially extending from edge 124 to edge 126. Referring to FIG. 6a, there is shown a sectional view taken along line 6—6 of FIG. 4a, illustrating that inner surface 122 and line 128 (drawn to connect inner edges 124, 126) form a second longitudinal passage 130 extending along longitudinal axis 102, and having a transverse cross sectional area 132. While FIGS. 4a, 4b and 6 illustrate transverse cross-sectional area 132 as being partially circular, like transverse cross-sectional area 112, other suitable geometric configurations are also contemplated. Important to the invention, transverse cross-sectional area 132 is less than transverse cross-sectional area 112. The importance of this variation in cross-sectional area will become apparent in later figures and related discussion. In a preferred embodiment, side wall 120 is a longitudinal continuation of a portion of side wall 108. Transverse cross-sectional area 132 is preferably longitudinally encompassed within transverse cross-sectional area 112.

Side wall 120 is circumferentially interrupted by longitudinal opening 134, extending along the entire length of distal portion 106 and extending across distal portion 106 from edge 124 to edge 126. Thus, the maximum width of second longitudinal passage 130 is defined as $W_1$. Important to the invention, maximum width $W_1$ is less than inner diameter $D_1$ of first longitudinal passage 110. Longitudinal opening 134 extends across a sector of the overall circumference of distal portion 106, subtending angle $\alpha$. In one form of the present invention, longitudinal opening 134 extends across about 180° ($\alpha$) of the overall circumference of distal portion 106, and maximum width $W_1$ is correspondingly greater than 0.500 of inner diameter $D_1$ of first longitudinal passage 110. In another form of the present invention, illustrated in FIG. 6b, longitudinal opening 134 extends across about 30° ($\alpha'$) of the overall circumference of distal portion 106, and maximum width $W_1'$ is correspondingly less than 0.986 of inner diameter $D_1$. In a preferred embodiment, the longitudinal opening extends across about 90° of the overall circumference of distal portion 106, and maximum width $W_1$ is correspondingly about 0.880 of inner diameter $D_1$. As will become apparent below, one of the purposes of distal portion 106 is to serve as a protective barrier between surgical tools and instrumentation (often having cutting edges) longitudinally advanced through guide sleeve 100, and delicate neural structures and bodily tissue located adjacent the outer surface of side wall 120.

Distal end 140 of distal portion 106 includes an elongated flange 142 projecting in a generally longitudinal direction and positioned generally opposite longitudinal opening 134. Elongated flange 142 has a height $H_2$ corresponding to a predetermined disc space between adjacent vertebrae. Insertion of elongated flange 142 within the disc space is typically required after distractor tip 74 has been extracted from the disc space in order to maintain the predetermined spacing. Elongated flange 142 has a length $L_1$ extending at least partially into the disc space to maintain distraction of the disc space, and to additionally provide protection to adjacent vessels and tissue, particularly the great blood vessel and various neurological structures. It should be understood that elongated flange height $H_2$ can be formed in various sizes and configurations depending upon the particular vertebral level being prepared for interbody fusion. Additionally, side walls 144 and 146 of elongated flange 142 can be tapered to conform to the normal anatomical angle between adjacent vertebral bodies. Distal end 148 of elongated flange 142 is preferably bullet-shaped to promote easy sliding of elongated flange 142 within the disc space and to avoid inadvertant damage to blood vessels, bodily tissue, or various neurological structures when elongated flange 142 is inserted within the disc space.

In one specific embodiment, distal end 140 of distal portion 106 includes a pair of engagement members 150 and 152, projecting in a generally longitudinal direction and diametrically oppositely disposed in a plane containing axis 102 and located between longitudinal opening 134 and elongated flange 142. Engagement members 150, 152 are preferably configured to penetrate at least partially into adjacent vertebral bodies to aid in maintaining the position of sleeve 100 relative to the disc space. One of engagement members 150, 152 is anchored in the upper vertebra while the other is anchored in the lower vertebra, thereby securing guide sleeve 100 in a desired position within the body. In one specific embodiment, engagement members 150, 152 are spiked protrusions having a sharp point 154 capable of penetrating into vertebral bone.

Proximal portion 104 of guide sleeve 100 includes an impactor head 156 configured to accept an impactor cap (not shown). Guide sleeve 100 is seated in position within the surgical site by impacting the impactor cap using a surgical mallet (not shown) until elongated flange 142 is positioned within the disc space, engagement members 150, 152 are driven into adjacent vertebrae, and distal end 140 of guide sleeve 100 is in contact with a surface of both of the vertebral bodies. Proximal portion 104 is also provided with a raised knurled portion 158 to allow the surgeon to securely grip and more easily manipulate guide sleeve 100 within and around the surgical site.

Figure 8:
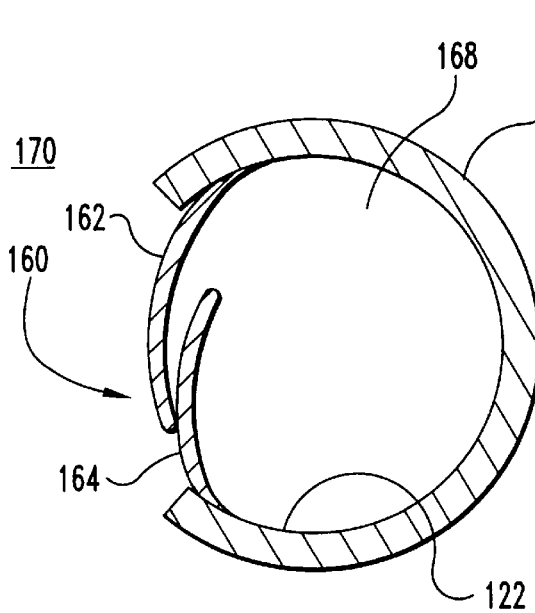
FIG. 8 is a sectional view taken along line 8—8 of FIG. 7a illustrating the retracted position of the protective barrier.
Figure 9:
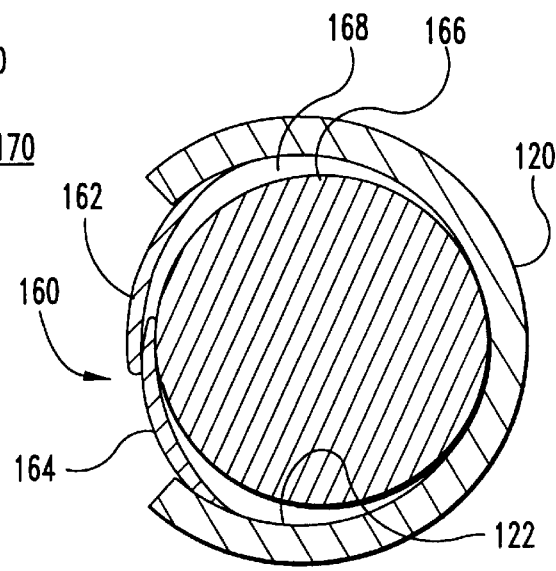
FIG. 9 is the sectional view of FIG. 8 illustrating the expanded position of the protective barrier when a surgical instrument is positioned within the protective guide sleeve.

Referring now to FIGS. 7a and 7b, there is shown an assembly in accordance with a further embodiment of the present invention utilizing guide sleeve 100 in combination with a protective barrier 160 positioned across longitudinal opening 134. Protective barrier 160 is provided to prevent possible damage to tissues which may invade the working channel within guide sleeve 100. Such tissue may be damaged by the operation, insertion, or removal of tools in the working channel. In the preferred embodiment, protective barrier 160 has a length sufficient to cover substantially the entire length of longitudinal opening 134, and is formed of a metallic material, such as, for example, surgical stainless steel. However, it is understood that protective barrier 160 can be formed from a variety of materials, including plastic. Referring to FIG. 8, there is shown a sectional view taken along line 8—8 of FIG. 7a, illustrating an embodiment of the present invention with protective barrier 160 shown in an initial retracted position. Protective barrier 160 preferably includes a pair of overlapping leaf members 162, 164 operably attached to inner surface 122 of side wall 120. It is understood that one leaf member can alternately be used to span across longitudinal opening 134 and that leaf members 162, 164 can be attached to guide sleeve 100 at a number of different locations using various means of attachment. Leaf members 162, 164 are relatively thin to allow for a certain degree of flexation. Leaf members 162, 164 also have an arcuate cross-section and preferably have an outer diameter approximately equal to the inner diameter of side wall 120. Referring to FIG. 9, there is shown an expanded operational position of protective barrier 160 when a surgical instrument 166 is positioned within guide sleeve 100. When surgical instrument 166 is longitudinally advanced through guide sleeve 100, leaf members 162, 164 expand out toward longitudinal opening 134 to provide an added degree of protection to bodily tissue or vessels laterally adjacent longitudinal opening 134. When surgical instrument 166 is removed from guide sleeve 100, leaf members 162, 164 retract back to their original position, as illustrated in FIG. 8. It should be understood that protective barrier 160 can take the form of various barrier means positioned across longitudinal opening 134 for separation of inner region 168 of guide sleeve 100 from the outside environment 170. For instance, protective barrier 160 can take the form of a flexible inner sleeve inserted within guide sleeve 100 or any other suitable structure capable of separating inner region 168 from outside environment 170 while providing an initial retracted position and a second expanded position relative to longitudinal opening 134.

Figure 10A:
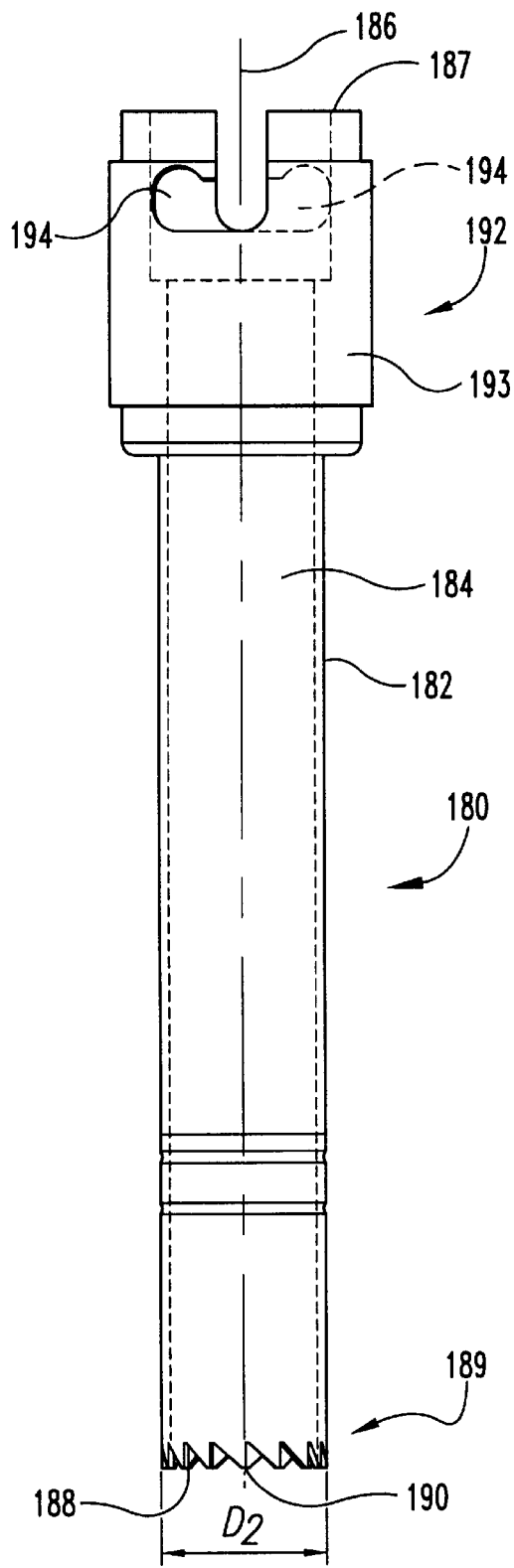
FIG. 10a is a side elevational view of a trephine.
Figure 10B:
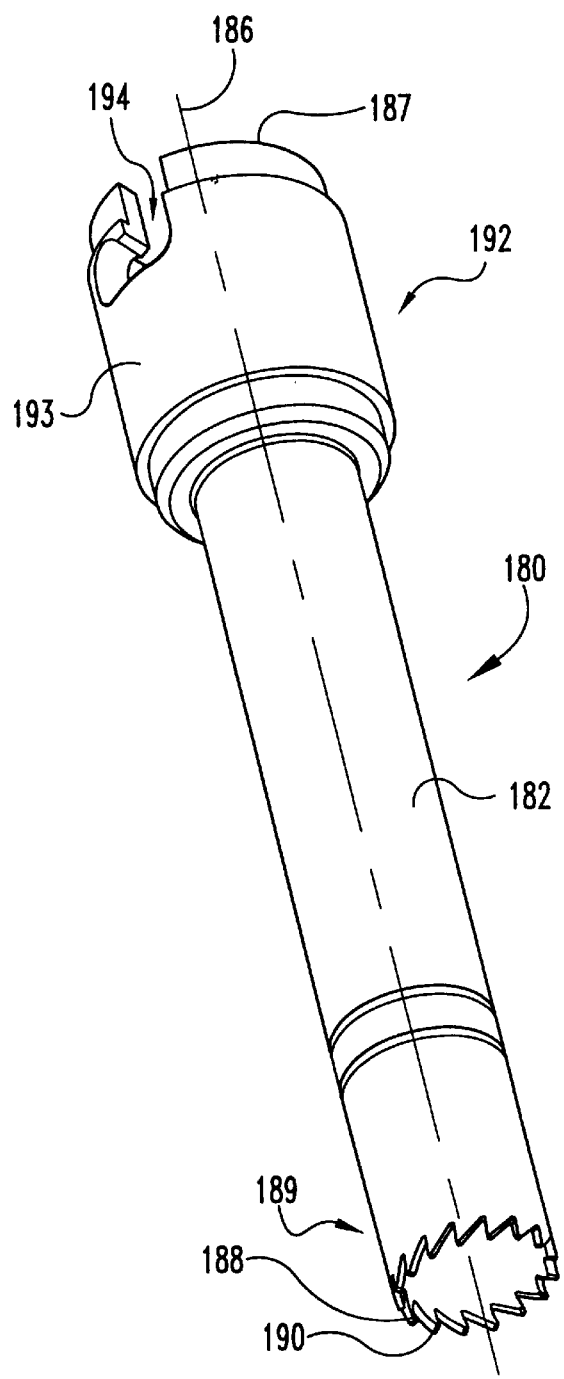

Referring now to FIGS. 10a and 10b, there is shown a trephine 180 used in combination with protective guide sleeve 100 to remove bodily tissue or vertebral bone in preparation for insertion of a bone dowel within the disc space. While a cylindrically-shaped trephine 180 is preferably used in combination with protective guide sleeve 100, the use of other configurations of cutting tools is also contemplated. Any suitable cutting tool capable of removing tissue or vertebral bone can be used, including rotary cutting tools such as a drill, drill tube planer or reamer. Trephine 180 is generally cylindrical and includes a side wall 182 defining a cannula 184 extending along longitudinal axis 186 from proximal end 187 to distal end 188. The distal portion of trephine 180 also includes a cutting head 189 defining a series of cutting teeth 190, projecting from distal end 188, to cut away tissue and bone material as trephine 180 is rotated about longitudinal axis 186. Cannula 184 thereby permits insertion of surgical instrumentation to easily remove the material disposed within the central area of cutting head 189. The proximal portion of trephine 180 includes a driving head 192 configured to accept either a power drill (not shown) or a conventional T-handle (not shown). Driving head 192 includes a knurled outer surface 193 to permit the surgeon to securely grasp and manipulate trephine 180 during the cutting operation. Driving head 192 also includes a pair of diametrically opposed slots 194, disposed clockwise from their longitudinally oriented rearward facing openings so as to engage diametrically opposing drive members (not shown) of a power drill or conventional T-handle.

As will be more fully described below, in an anticipated method of the present invention, trephine 180 is positioned within guide sleeve 100 to remove tissue and bone extending into the interior of guide sleeve 100 through longitudinal opening 134. Thus, the outer diameter $D_2$ of cutting head 189 is sized slightly smaller than inner diameter $D_1$ of first longitudinal passage 110 of guide sleeve 100 to allow trephine 180 to be slidably received within guide sleeve 100. Side wall 182 preferably has an outer diameter $D_2$ sized in close tolerance to inner diameter $D_1$ of first longitudinal passage 110 to effectively guide trephine 180 along longitudinal axis 102 of guide sleeve 100.

Referring now to FIGS. 11–17, shown therein is a preferred surgical method for preparing an upper and lower vertebra and the disc space therebetween for implantation of a bone dowel into the disc space using a posterior surgical approach. Once a surgeon has identified the two vertebrae which are to be fused, the surgeon then determines the desired amount of distraction required between the vertebrae to accommodate insertion of the bone dowel.

Figure 11:
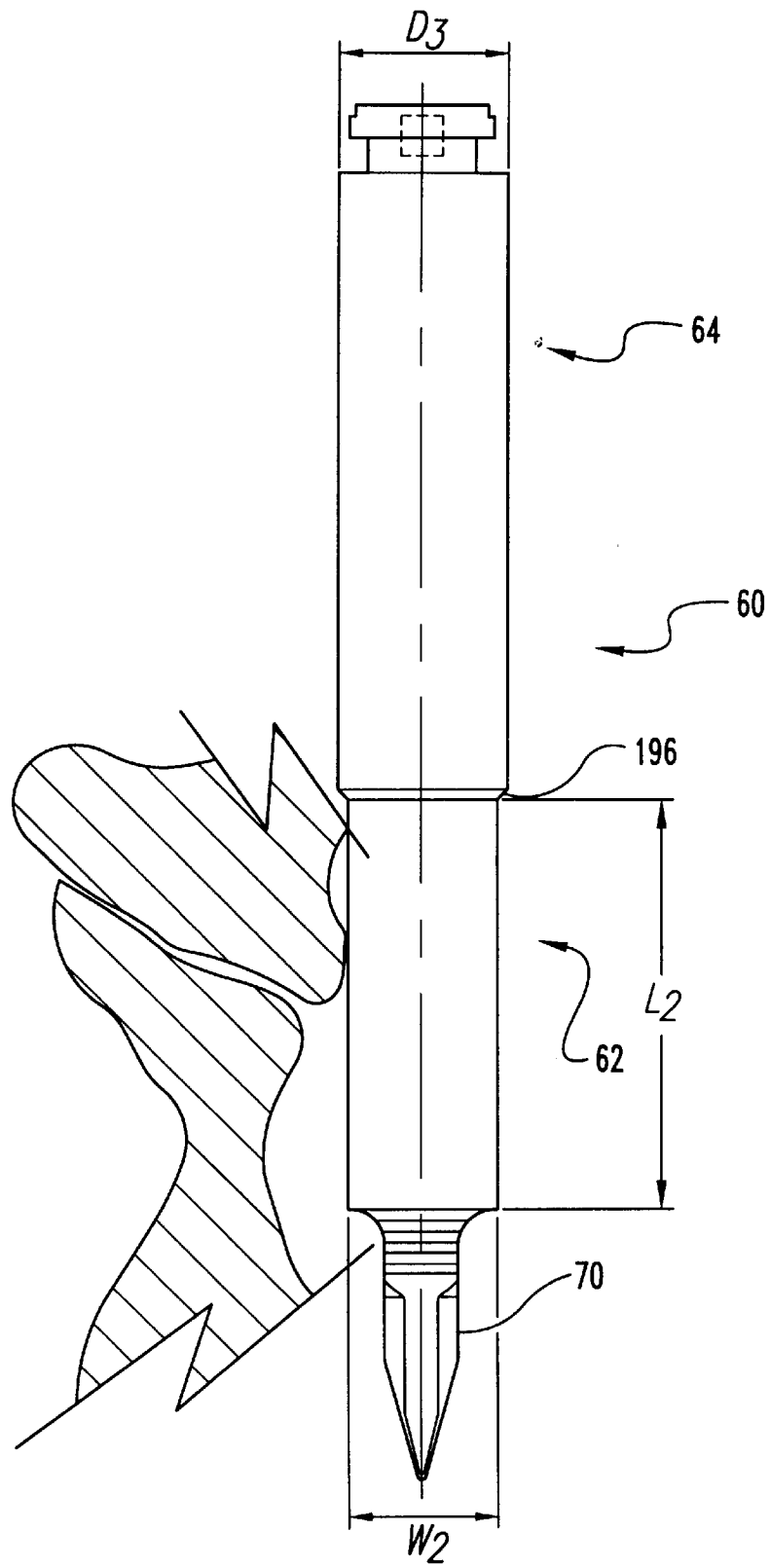
FIG. 11 is a side elevational view of the distractor of FIGS. 3a and 3b inserted into the interdiscal region of the spine near the facet joint of two adjacent vertebrae.

Referring to FIG. 11, there is shown spinal distractor 60 inserted into the interdiscal region of the spine near the facet joint of two adjacent vertebrae. As described above, distractor tip 70 is designed such that it can be inserted into a disc space to provide a predetermined spacing between adjacent vertebrae. As illustrated, leading portion 62 has a reduced cross section relative to trailing portion 64 and has a length $L_2$. Leading portion 62 is configured such that a minimal amount of facet and upper lamina bone and tissue must be removed to accommodate the distraction process. Specifically, the reduced cross section of leading portion 62 has a width $W_2$ and a sufficient length $L_2$ to avoid, or at the very least minimize, the amount of bone and tissue removal required to allow passage of spinal distractor 60 within the surgical site during the distraction of the disc space. Leading portion 62 transitions into trailing portion 64 at transition area 196. Trailing portion 64 has an outer diameter $D_3$ which is sized slightly smaller and in close tolerance to inner diameter $D_1$ of first longitudinal passage 110 of guide sleeve 100.

Figure 12:
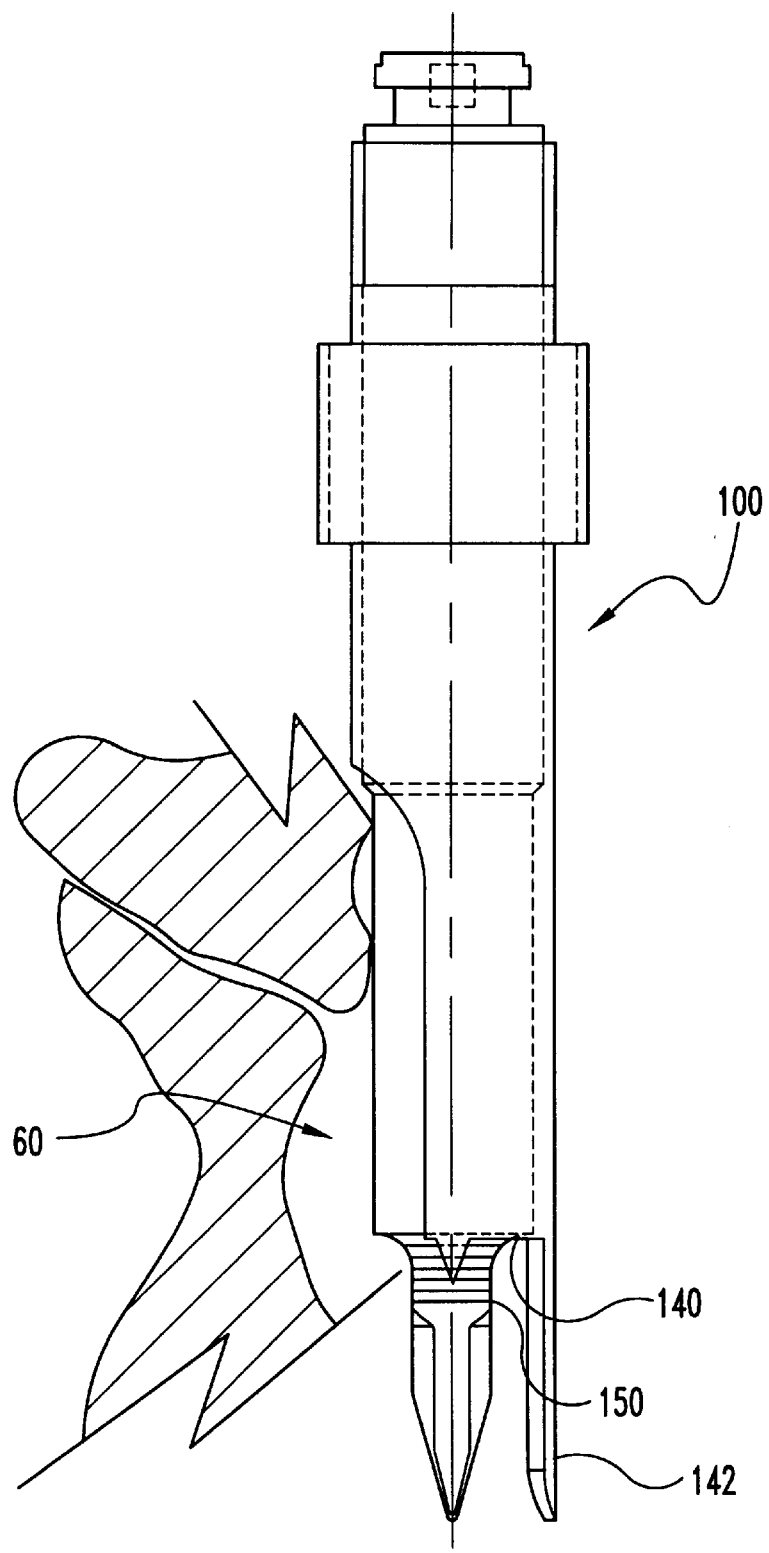
FIG. 12 is a side elevational view of the protective guide sleeve of FIGS. 4a and 4b positioned over the distractor of FIGS. 3a and 3b.

Referring to FIG. 12, there is shown guide sleeve 100 positioned over spinal distractor 60. Guide sleeve 100 is aligned such that longitudinal opening 134 is positioned toward the facet joint of the upper and lower vertebrae and generally opposite the dural region of the spine. Longitudinal opening 134 is sufficiently sized to avoid having to remove any more vertebral bone or tissue than that already required to accommodate insertion of spinal distractor 60. As mentioned above, outer diameter $D_3$ of trailing portion 64 is sized slightly smaller than inner diameter $D_1$ of first longitudinal passage 100. Trailing portion 64 thus serves as both a centering post and an alignment rod for the subsequent insertion of guide sleeve 100 to thereby assure proper alignment of guide sleeve 100 relative to the disc space. Guide sleeve 100 is then seated in position within the surgical site by impacting the impactor cap (not shown) using a surgical mallet until elongated flange 142 is positioned within the disc space, engagement members 150 and 152 are driven into the adjacent vertebrae, and distal end 140 is completely in contact with a surface of both vertebral bodies. With guide sleeve 100 firmly seated in position relative to the disc space, spinal distractor 60 can be extracted from the disc space using an extractor (not shown) and slidably removed from the interior of guide sleeve 100. The combination of elongated flange 142 and engagement members 150, 152 rigidly secure guide sleeve 100 in position and thereby assure the precise alignment of surgical tools and instrumentation relative to the disc space during subsequent steps of the implantation process.

Figure 13:
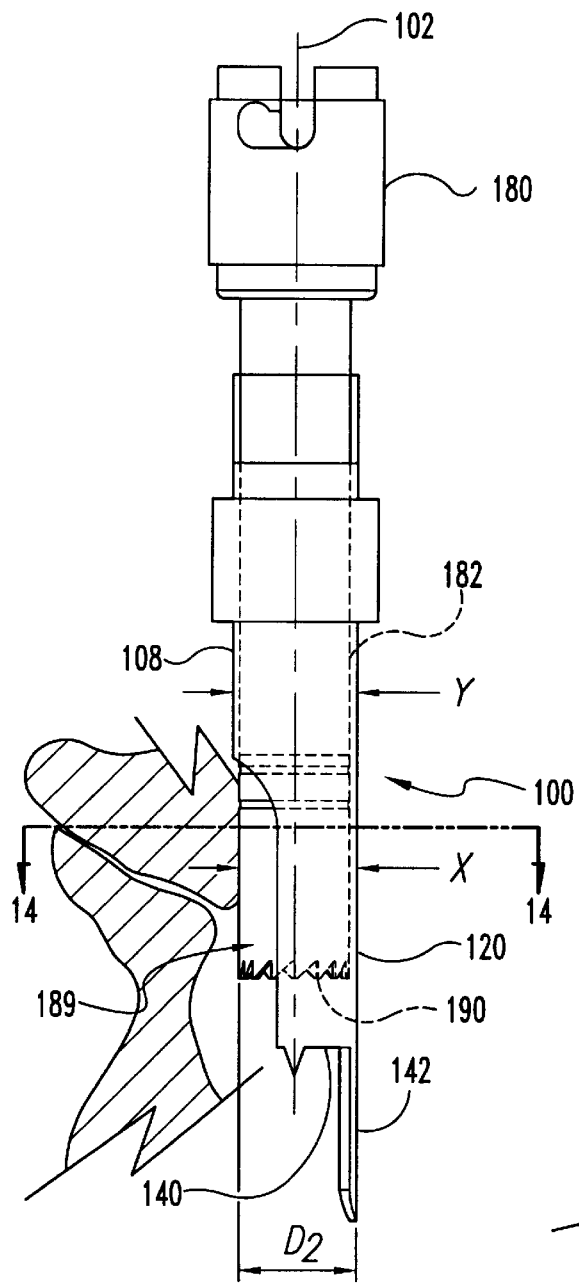
FIG. 13 is a side elevational view of the trephine of FIGS. 10a and 10b positioned within the protective guide sleeve of FIGS. 4a and 4b.

Referring now to FIG. 13, there is shown trephine 180 positioned within guide sleeve 100. It is understood that the process of trephining is only required if bone or tissue extends into the interior of guide sleeve 100 through longitudinal opening 134, thereby requiring removal to accommodate for the insertion of bone dowel 8 through guide sleeve 100 and into the disc space. As mentioned above, outer diameter $D_2$ of cutting head 189 is sized to have a close tolerance with the inner diameter $D_1$ of first longitudinal passage 110 of guide sleeve 100.

As a result, trephine 180 can rotate within first longitudinal passage 110 and move axially relative thereto, but cannot move laterally relative to guide sleeve 100, thus insuring the precise and accurate removal of bone and tissue extending through longitudinal opening 134. Preferably, side wall 182 of trephine 180 has an outer diameter $D_2$ to further aid in guiding cutting head 189 along longitudinal axis 102 of guide sleeve 100.

As trephine 180 is axial advanced through guide sleeve 100, cutting head 189 will thereby remove tissue laterally extending into the interior of guide sleeve 100 through longitudinal opening 134. In one embodiment, the tissue removed by cutting head 189 is vertebral bone. In another embodiment, the vertebral bone removed by cutting head 189 is bony facet material. In yet another embodiment, cutting head 189 simultaneously removes vertebral bone and facet material from the upper and lower vertebrae. Trephine 180 is axially advanced through guide sleeve 100 until cutting teeth 190 are approximately adjacent or co-planar with distal end 140 of guide sleeve 100. The trephining process thereby allows for the precise removal of vertebral bone and facet structure necessary to allow passage of a bone dowel having a maximum diameter slightly smaller than diameter $D_2$ of cutting head 189.

As illustrated by FIGS. 12 and 13, the open portion of side wall 120 of guide sleeve 100 minimizes the working space required for preparation of the surgical site for insertion of a bone dowel. The trephining process subsequently provides the full diameter of exposure necessary for the later steps of reaming, tapping, and insertion of the bone dowel (to be discussed in detail below). Thus, the insertion of a bone dowel having a maximum diameter slightly smaller than diameter $D_2$ requires a maximum exposure width X. This compares to a maximum exposure width Y required of conventional guide sleeves having a continuous, uninterrupted side wall.

By way of example, and not in any way limiting the scope of the present invention, with conventional guide sleeves having a 1 mm side wall, a bone dowel having a maximum diameter of 16 mm would require a maximum exposure width X of 18 mm. However, with the guide sleeve of the present invention (having a portion of side wall 120 removed), the maximum exposure width X is only 17 mm. Thus, approximately 1 mm less bone removal is required if guide sleeve 100 is used in the place of a conventional guide sleeve. Regardless of the size of the bone dowel, the guide sleeve of the present invention will result in a lesser amount of vertebral facet joint bone removal than that required of conventional guide sleeves. More specifically, the amount of bone removal will be lessened by an amount approximately equal to the thickness of the guide sleeve side wall. Importantly, as noted above, the decreased and precise removal of vertebral bone translates into increased stability of the spinal posterior column.

To more fully describe the trephining process, reference will now be made to FIGS. 4a–b, 5, 6a and 13. As discussed above, guide sleeve 100 defines a first longitudinal passage 110 having a transverse cross sectional area 112 and a second longitudinal passage 130 having a transverse cross sectional areas 132. As also described above, transverse cross sectional area 132 is less than transverse cross sectional area 112. Side wall 182 of trephine 180 is sized to be accepted in close tolerance within first longitudinal passage 110 and has a transverse cross sectional area corresponding to that of transverse cross sectional area 112. As trephine 180 is advanced through guide sleeve 100 along longitudinal axis 102, tissue may be removed from an area laterally adjacent second longitudinal passage 130. More specifically, tissue within the area adjacent second longitudinal passage 130 and longitudinally encompassed within transverse cross sectional area 112 may thereby be removed. In other words, tissue laterally extending into the interior of guide sleeve 100 through longitudinal opening 134 is subject to removal. The important of the variation in transverse cross sectional areas 112, 132 is thereby readily apparent. Correspondingly, it is also apparent why maximum width $W_1$ of second longitudinal passage 130 must be less than inner diameter $D_1$ of first longitudinal passage 110. Namely, a portion of side wall 120 is removed to provide maximum width $W_1$, thereby allowing cutting head 189 having a diameter $D_2$ slightly less than inner diameter $D_1$ to remove tissue extending through longitudinal opening 134.

Figure 14:
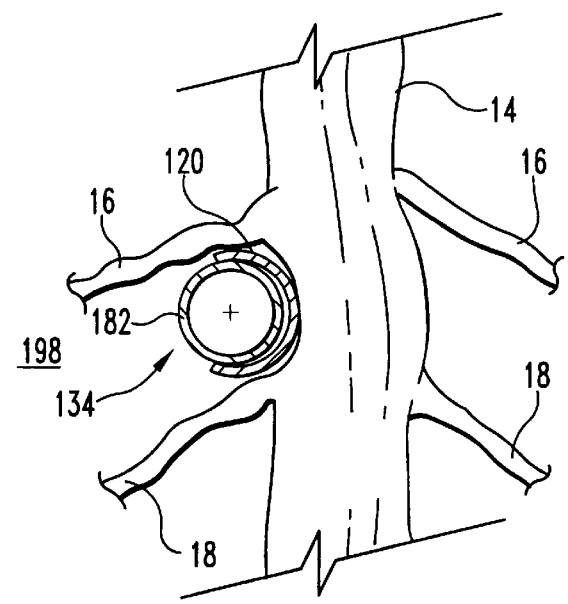
FIG. 14 is a sectional view taken along line 14—14 of FIG. 13 illustrating the position of the protective guide sleeve relative to the neural structures of the spine, with the vertebral structures of the spine not shown for clarity.

Referring now to FIG. 14, there is shown side wall 182 of trephine 180 positioned within guide sleeve 100 adjacent side wall 120. The assembly illustrates the position of guide sleeve 100 relative to the delicate neurological structures of the spine. As shown, longitudinal opening 134 of guide sleeve 100 is positioned generally opposite the dural region of the spine. Importantly, all of the delicate neurological structures are located medial or superior/inferior longitudinal opening 134. Specifically, the dura 14 is located directly medial longitudinal opening 134 while upper and lower nerve roots 16, 18 are respectively located superior and inferior longitudinal opening 134. No neural structures are located directly lateral longitudinal opening 134, thereby creating a safe zone 198 requiring a lesser degree of protection than the surrounding adjacent areas. Thus, side wall 120 of guide sleeve 100 provides protection of tissue and delicate neurological structures from damage by surgical instrumentation and tools, such as trephine 180, while allowing removal of tissue and bone generally located within safe zone 198, but only to the extent that it extends into the interior of guide sleeve 100 through longitudinal opening 134.

Figure 15:
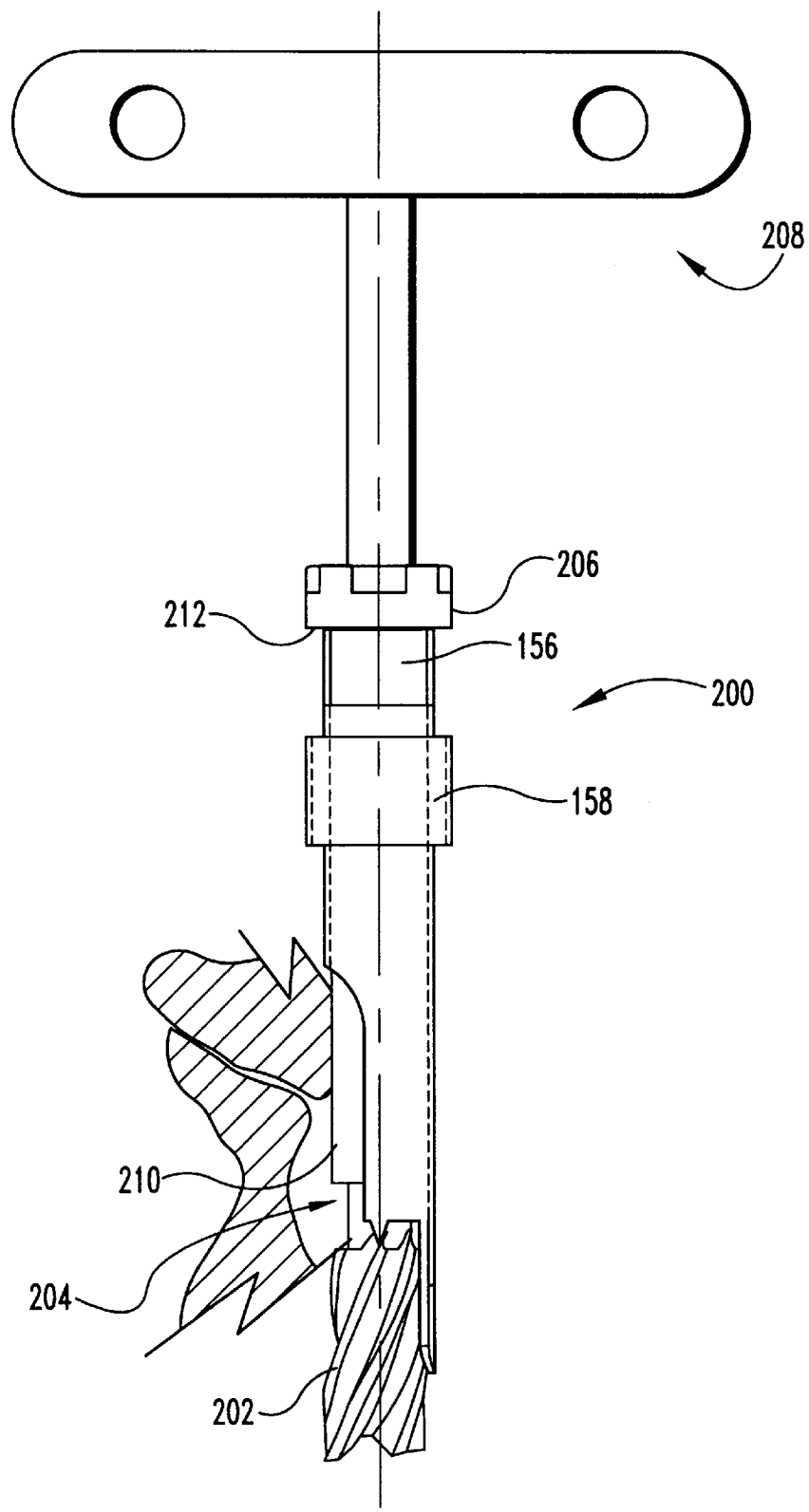
FIG. 15 is a side elevational view of a reamer positioned within the protective guide sleeve of FIGS. 4a and 4b.

Referring now to FIG. 15, there is shown a reamer 200 positioned within guide sleeve 100. Reamer 200 includes a cutting head 202, a shaft 204, a spacer ring 206 and a T-handle 208. Shaft 204 includes a larger diameter portion 210 sized to have a reasonably close fit within first longitudinal passage 110 of guide sleeve 100 to permit rotation of the device, yet limit the amount of transverse movement within guide sleeve 100 to insure precise and accurate reaming of the disc space. Cutting head 202 is operatively joined to the distal end of shaft 204 and sized slightly larger than the outer diameter of the bone dowel if a smooth bone dowel is used, or alternately sized slightly smaller than the root diameter of a threaded bone dowel to accommodate for the cutting of female threads within the implant bore. Formed on the proximal end of shaft 204 is a Hudson-type connection for engagement with T-handle 208 or other alternate handle configurations. Spacer ring 206 cooperates with and is releasably fastened to shaft 204 to provide a depth stop to prevent the overpenetration of reamer 200 beyond the disc space. Overpenetration of cutting head 202 beyond the disc space could possibly result in paraplegia or a life-threatening perforation of the aorta, vena cava, or iliac vessels. Spacer ring 206 includes an abutment shoulder 212 which engages the proximal end of guide sleeve 100 and prevents further advancement of reamer 200 within the disc space. As illustrated in FIG. 15, reamer 200 is inserted through and guided by guide sleeve 100 and removes relatively equal amounts of bone material from both the upper and lower vertebrae to thereby form an implant bore within the disc space. As in the trephining process, guide sleeve 100 also serves to protect tissue and neural structures from the sharp cutting edges of cutting head 202. Typically, a minimum of three reaming sequences are needed to adequately extract the bone and disc debris. Thereafter, reamer 200 is slidably removed from the disc space and guide sleeve 100, thereby leaving a relatively smooth implant bore.

Figure 16:
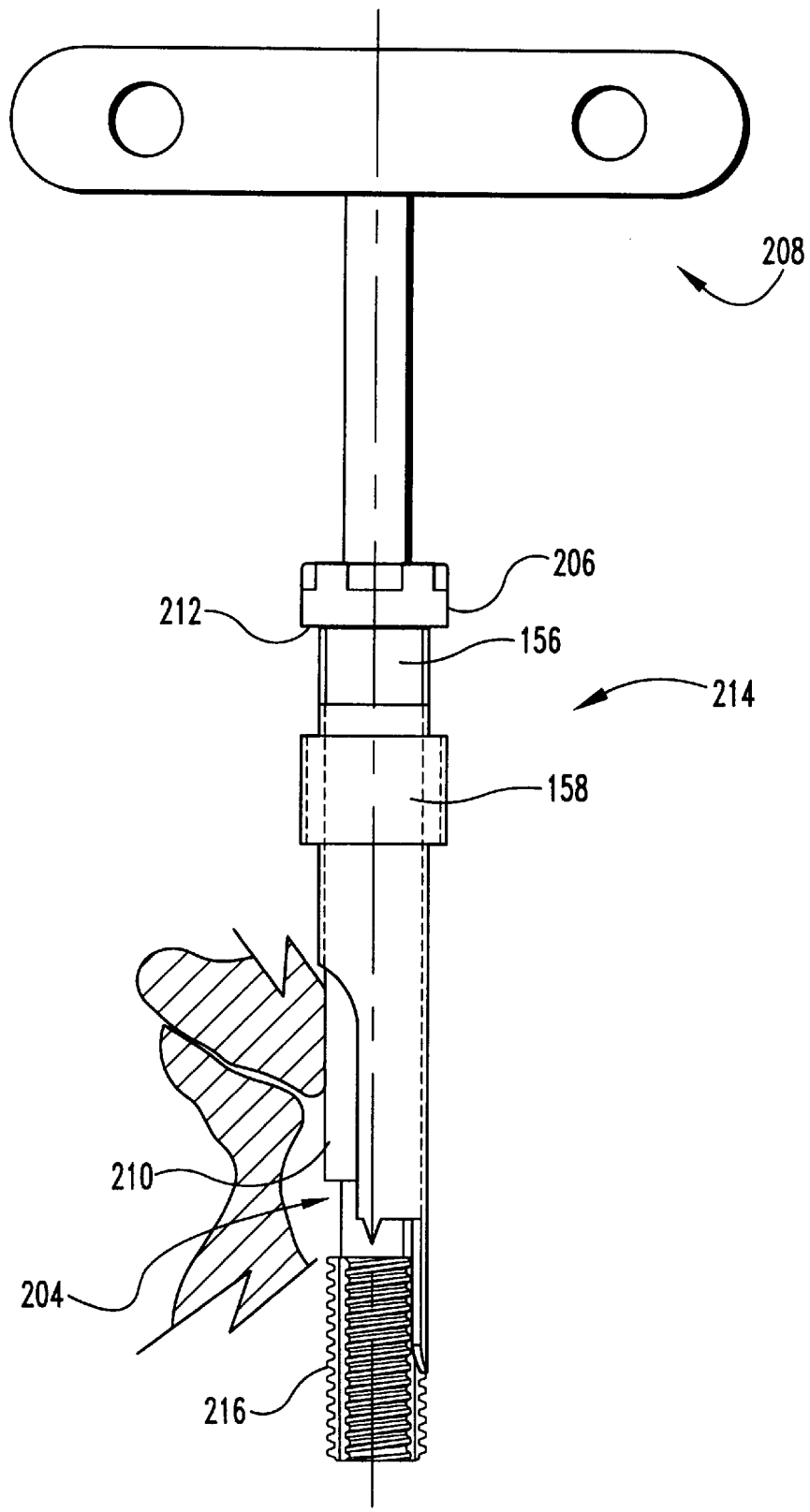
FIG. 16 is a side elevational view of a bone tap positioned within the protective guide sleeve of FIGS. 4a and 4b.

Referring to FIG. 16, there is shown a bone tap 214 positioned within guide sleeve 100. It is understood that the process of tapping is only required if the bone dowel implant is threaded. Bone tap 214 is configured similarly to reamer 200, including a shaft 204, a spacer ring 206 and a T-handle 208. Shaft 204 also includes a larger diameter portion 210 sized to permit rotation of bone tap 214, yet maintain the axial alignment of bone tap 214 within guide sleeve 100 to ensure the precise cutting of internal threads within the implant bore corresponding to the external threads of the bone dowel. Spacer ring 206 similarly prevents the overpenetration of tap head 216 beyond the implant bore. As illustrated in FIG. 16, bone tap 214 is inserted through and guided by guide sleeve 100 to thereby tap female threads within the implant bore. Bone tap 214 is then removed from guide sleeve 100, thereby completing preparation of the disc space to receive a threaded bone dowel.

Referring to FIG. 17, there is shown a bone dowel holder 220 positioned within guide sleeve 100. Releasably attached to bone dowel holder 220 is bone dowel 8. Bone dowel holder 220 includes an engagement head 222, a hollow outer shaft 224, a spacer ring 226, and a handle portion 228. Bone dowel holder 220 also includes an inner shaft (not shown) having a threaded distal end for engaging an internally threaded portion of bone dowel 8. The inner shaft also has a proximal end which is joined to a thumb wheel 230 for providing rotation of the inner shaft relative to outer shaft 224 for releasably engaging bone dowel 8. The distal end of outer shaft 224 includes an engagement tip (not shown) which mates with an engaging slot formed in bone dowel 8 for driving bone dowel 8 into the threaded implant bore within the disc space. Outer shaft 224 has an outer diameter sized to have a reasonably close fit within first longitudinal passage 110 of guide sleeve 100 to permit rotation of bone dowel holder 220, yet maintain the axial alignment of outer shaft 224 within guide sleeve 100 to ensure the precise threading of bone dowel 8 within the threaded implant bore. Spacer ring 226 prevents the overpenetration of bone dowel 8 beyond the implant bore. Formed on the proximal end of outer shaft 224 is a Hudson-type connection for engagement with T-handle 234 or other alternate handle configurations. As illustrated in FIG. 17, bone dowel 8 is threaded onto the distal end of the inner shaft of bone dowel holder 200 with the engagement tip positioned within the bone dowel engaging slot. Bone dowel holder 220 and bone dowel 8 are then inserted through and guided by guide sleeve 100. Bone dowel 8 is then threaded into the threaded implant bore by rotating T-handle 234 in a clockwise direction. Once bone dowel 8 is positioned within the disc space, thumb-wheel 230 is rotated in a counter-clockwise direction to disengage bone dowel 8 from the distal end of the inner shaft. Thereafter, bone dowel holder 220 is removed from guide sleeve 100 followed by the removal of guide sleeve 100 from the surgical site.

Referring now to FIG. 18, there is shown a portion of the lumbar region of the spinal column demonstrating the end result of the posterior interbody fusion technique of the present invention. As is clearly illustrated by a comparison of FIGS. 1 and 18, the instrumentation and technique of the present invention, as shown in FIG. 18, requires minimal removal of vertebral bony structures in order to accommodate insertion of bone dowels 8 within the disc space. Only the precise amount of bone material is removed from upper vertebra L4 and lower vertebra L5 to allow for the implantation of bone dowels 8. By limiting the amount of vertebral bone material from the spinal posterior column, the overall stability of the spine will thereby be significantly increased. Furthermore, larger diameter bone dowels can be used without drastically affecting the stability of the spine. The placement of larger diameter bone dowels also results in greater intradiscal distraction and tensioning of the annulus and provides a larger surface area of engagement between the bone dowel and the adjacent vertebrae. The larger surface area of engagement results in greater stability and an increased likelihood of interbody fusion.

While a posterior approach has been described in detail, it should be understood that the present invention can be used in an anterior approach for both laparscopic or non-laparscopic procedures.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A guide used in conjunction with the preparation of a vertebral body for spinal surgery, comprising:
   a sleeve defining a longitudinal axis and having a body;
   said body defining a first longitudinal passage having a first transverse cross sectional area;
   said body also defining a second longitudinal passage having a second transverse cross sectional area, said second longitudinal passage in communication with said first longitudinal passage, said second transverse cross sectional area being less than said first transverse cross sectional area; and
   said sleeve is positionable adjacent the vertebral body to allow removal of vertebral tissue laterally adjacent said second longitudinal passage by an axially displacable cutting tool extending through said first longitudinal passage.

2. The guide of claim 1 wherein said first longitudinal passage is sized to guide said cutting tool generally along said longitudinal axis.

3. The guide of claim 1 wherein said first transverse cross sectional area is generally circular.

4. The guide of claim 1 wherein said second transverse cross sectional area is partially circular.

5. A guide used in conjunction with the preparation of a vertebral body for spinal surgery, comprising:
   a sleeve defining a longitudinal axis and having a cylindrical side wall;
   said side wall including a circumferentially uninterrupted portion defining a first longitudinal passage having a diameter;
   said side wall also including a circumferentially interrupted portion defining a second longitudinal passage having a maximum width, said width being less than said diameter; and
   wherein said sleeve is positionable adjacent the vertebral body to allow removal of vertebral tissue laterally adjacent said second longitudinal passage by an axially displacable cutting tool extending through said first longitudinal passage.

6. The guide of claim 5 wherein said diameter of said first longitudinal passage being sized to guide said cutting tool generally along said longitudinal axis.

7. The guide of claim 5 wherein a spinal implant is guidable through said sleeve generally along said longitudinal axis, the implant having an outer diameter substantially equal to said diameter of said first longitudinal passage.

8. A guide used in conjunction with the preparation of a vertebral body for spinal surgery, comprising:
   a sleeve defining a longitudinal axis and having a proximal portion and an opposing distal portion, said proximal portion having a continuous side wall, said distal portion having a side wall defining an opening extending longitudinally from a distal end of said sleeve toward said proximal portion, said distal portion being positionable adjacent the vertebral body with vertebral tissue extending transversely into said opening.

9. The guide of claim 8 wherein said sleeve includes an elongated flange projecting from said distal end and positioned generally opposite said opening.

10. The guide of claim 9 therein said flange is configured to be slidably received within the disc space between two adjacent vertebrae to maintain a predetermined spacing between said vertebrae.

11. The guide of claim 10 wherein said sleeve includes at least two engagement members extending longitudinally from said distal end.

12. The guide of claim 11 wherein said engagement members are spiked protrusions.

13. The guide of claim 8 wherein said distal portion defines an interior, said opening being in communication with said interior with vertebral tissue extending transversely through said opening and into said interior, the vertebral tissue within said interior being removable by an axially displacable cutting tool.

14. A guide used in conjunction with spinal surgery, comprising:
   a sleeve defining a longitudinal axis and having a proximal portion and an opposing distal portion, said proximal portion having a continuous side wall, said distal portion having a side wall defining an opening extending longitudinally from a distal end of said sleeve toward said proximal portion, said sleeve including a protective barrier positioned across at least a portion of said opening.

15. The guide of claim 14 wherein said protective barrier includes at least one flexible leaf member operably attached to said sleeve.

16. The guide of claim 15 wherein said protective barrier includes a pair of overlapping, flexible leaf members operably attached to said sleeve.

17. The guide of claim 14 wherein said protective barrier is metallic.

18. A guide used in conjunction with spinal surgery, comprising:

a sleeve defining a longitudinal axis and having a proximal portion and an opposing distal portion, said proximal portion having an uninterrupted side wall, said distal portion having a side wall defining an opening extending longitudinally along the entire length of said distal portion, said sleeve including a barrier means positioned across said opening for separating an inner region of said sleeve from the outer environment; and retention means for retaining adjacent vertebra in position relative to said sleeve.

19. A guide used in conjunction with the preparation of a vertebral body for spinal surgery comprising:

a sleeve defining a longitudinal axis and having a cylindrical side wall;

said side wall including a circumferentially uninterrupted portion; and said side wall also including a circumferentially interrupted portion defining an opening extending longitudinally from a distal end of said circumferentially interrupted portion toward said circumferentially uninterrupted portion, said circumferentially interrupted being positionable adjacent the vertebral body with vertebral tissue extending transversely into said opening.

20. The guide of claim 19 wherein said opening extends across greater than about 30 degrees of the overall circumference of said circumferentially interrupted portion.

21. The guide of claim 19 wherein said opening extends across less than about 180 degrees of the overall circumference of said circumferentially interrupted portion.

22. The guide of claim 19 wherein said opening extends across a range of about 30 degrees to 180 degrees of the overall circumference of said circumferentially interrupted portion.

23. The guide of claim 22 wherein said opening extends across about 90 degrees of the overall circumference of said circumferentially interrupted portion.

24. The guide of claim 19 wherein said sleeve is used to guide a spinal implant generally along the longitudinal axis, said circumferentially interrupted portion having an inner diameter, the implant having a maximum outer diameter substantially equal to said inner diameter.

25. The guide of claim 24 wherein said spinal implant is a cylindrically shaped bone dowel.

26. The guide of claim 19 wherein said circumferentially interrupted portion defines an interior, said opening being in communication with said interior with vertebral tissue extending transversely through said opening and into said interior, the vertebral tissue within said interior being removable by an axially displacable cutting tool.

27. A guide used in conjunction with the preparation of a vertebral body for spinal surgery, comprising:

a sleeve defining a longitudinal axis and having a guiding portion defining an uninterrupted inner guiding surface and a protecting portion including a protective side wall defining an opening extending longitudinally from a distal end of said protecting portion toward said guiding portion, said protecting portion being positioned adjacent the vertebral body with vertebral tissue extending transversely into said opening.

28. The guide of claim 27 wherein said protecting portion includes an elongated flange projecting from said distal end in a longitudinal direction and positioned generally opposite said opening.

29. The guide of claim 28 wherein said flange is configured to be slidably received within a disc space between two adjacent vertebrae to maintain a predetermined spacing between said vertebrae.

30. The guide of claim 27 wherein said protecting portion includes at least two engagement members projecting from said distal end in a longitudinal direction for anchoring said sleeve to vertebral bone.

31. The guide of claim 30 wherein said engagement members are spiked protrusions.

32. The guide of claim 22 wherein said inner guiding surface is configured to guide surgical tools through said sleeve generally along said longitudinal axis.

33. The guide of claim 27 wherein said protective side wall is positioned adjacent the dural region of the spine.

34. The guide of claim 27 wherein said sleeve is used to guide a spinal implant generally along the longitudinal axis, said protective side wall having an inner diameter, the implant having an outer diameter substantially equal to said inner diameter.

35. A system for lateral removal of tissue in preparation for spinal surgery, comprising:

a sleeve defining a longitudinal axis and having a side wall, said side wall defining a first longitudinal passage and a second longitudinal passage; and a cutting tool sized to be received within said first longitudinal passage and having a cutting end for removal of tissue laterally adjacent said second longitudinal passage when said cutting end is axially displaced generally along said longitudinal axis.

36. The system of claim 35 wherein said cutting tool is a rotary cutting tool.

37. The system of claim 36 wherein said rotary cutting tool is a trephine.

38. The system of claim 36 wherein said first longitudinal passage has a generally circular cross section and is sized to receive and guide said rotary cutting tool through said sleeve generally along said longitudinal axis.

39. The system of claim 38 wherein said rotary cutting tool is a trephine.

40. The system of claim 35 further including a spinal distractor having a leading portion and a trailing portion, said trailing portion having an outer diameter sized to be slidably received within said first longitudinal passage, said leading portion having a reduced outer cross section relative to said trailing portion.

41. A guide used in conjunction with spinal surgery comprising:

a sleeve having a cylindrical side wall;

said side wall including a circumferentially uninterrupted portion, said side wall also including a circumferentially interrupted portion defining an opening extending along the entire length of said circumferentially interrupted portion;

an elongated flange projecting from the end of said circumferentially interrupted portion and positioned generally opposite said opening; and a protective barrier positioned across said opening.

42. The guide of claim 41 wherein said protective barrier includes at least one flexible leaf member operably attached to said sleeve.

43. The guide of claim 42 wherein said protective barrier includes a pair of overlapping, flexible leaf members operably attached to said side wall.

44. The guide of claim 41 wherein said protective barrier is metallic.

45. A guide sleeve for placement of a spinal implant within a disc space between an upper vertebral surface and a lower vertebral surface, comprising:

a proximal portion extending along a longitudinal axis and having an uninterrupted side wall;

a distal portion extending along said longitudinal axis and having a side wall defining an interior sized to receive the spinal implant therethrough, said side wall defining an opening extending in a longitudinal direction from a distal end of said distal portion toward said proximal portion and in communication with said interior, said opening being positioned adjacent a lateral vertebral surface with vertebral tissue extending transversely into said opening; and a distracting portion comprising an elongated flange projecting from said distal end in a longitudinal direction and having a height corresponding to said disc space, said flange projecting between said upper and lower vertebral surface to maintain distraction of said disc space.

46. The guide sleeve of claim 45 wherein said side wall is a partial cylinder defining an inner diameter, the spinal implant having an outer diameter substantially equal to said inner diameter.

47. The guide sleeve of claim 45 wherein said opening is positioned generally opposite the dural region of the spine.

48. A surgical method for implanting a spinal implant into a disc space between an upper and a lower vertebra, comprising:

providing a boring tool and a guide sleeve defining a longitudinal axis and having a proximal portion and an opposing distal portion, said proximal portion having an uninterrupted side wall, said distal portion having a side wall defining an opening extending in a longitudinal direction from a distal end of said sleeve toward said proximal portion;

positioning the distal portion adjacent a vertebral body with vertebral tissue extending transversely into the opening;

inserting the boring tool through the guide sleeve and forming an implant bore within the disc space;

removing the boring tool from the guide sleeve;

inserting a spinal implant through the guide sleeve and implanting the spinal implant into the implant bore; and removing the guide sleeve.

49. The surgical method of claim 48 wherein the opening is in communication with an interior of said distal portion of said guide sleeve; and further including inserting a cutting tool through the guide sleeve and removing vertebral tissue extending into the interior of the guide sleeve prior to forming the implant bore.

50. The surgical method of claim 48 further including inserting a tapping tool through the guide sleeve to tap a female thread within the implant bore prior to inserting and implanting the spinal implant.

51. The surgical method of claim 48 including positioning a protective barrier across the opening.

52. The surgical method of claim 51 further including expanding the protective barrier during the inserting of the boring tool or spinal implant.

53. The surgical method of claim 48 wherein the guide sleeve has at least two engagement members projecting from the distal end of the distal portion, and wherein the surgical method further includes anchoring at least one of the engagement members into each of the upper and lower vertebra.

54. The surgical method of claim 48 wherein the guide sleeve has an elongated flange projecting from the distal end of the distal portion, the flange having a width approximately equal to the predetermined spacing between the upper and lower vertebrae and positioned generally opposite the opening, and wherein the surgical method further includes positioning the flange between the upper and lower vertebrae.

55. The surgical method of claim 48 wherein the side wall of the distal portion has an inner diameter, the spinal implant having an outer diameter substantially equal to the inner diameter.

56. The surgical method of claim 48 wherein said opening is positioned generally opposite the dural region of the spine.

57. The surgical method of claim 48 further comprising:

providing a spinal distractor;

inserting the distractor into the disc space to spread apart the upper and lower vertebra to a predetermined spacing;

placing the guide sleeve over the distractor with the opening positioned generally opposite the dural region of the spine; and extracting the distractor from the disc space prior to inserting the boring tool.

58. The surgical method of claim 57 wherein the spinal distractor includes a leading portion and a trailing portion, the trailing portion having an outer diameter slightly less than the inner diameter of the proximal portion of the guide sleeve, the leading portion having a reduced outer cross section relative to the trailing portion.

59. A surgical method for preparing an upper and lower vertebra for implantation of a spinal implant into the disc space, comprising:

providing a cutting tool and a guide sleeve defining a longitudinal axis and having a proximal portion and an opposing distal portion, said proximal portion having an uninterrupted side wall, said distal portion having a side wall defining an interior and an opening extending in a longitudinal direction from a distal end of the sleeve toward the proximal portion and in communication the interior;

positioning the distal portion adjacent a vertebral body with vertebral tissue extending transversely thorough the opening and into the interior of the distal portion; and inserting the cutting tool through the guide sleeve to remove the vertebral tissue extending into the interior of the distal portion.

60. The surgical method of claim 59 wherein the tissue extending into the interior of the distal portion is vertebral bone.

61. The surgical method of claim 60 wherein the vertebral bone is facet material.

62. The surgical method of claim 59 wherein the removing of the vertebral tissue extending into the interior of the distal portion includes the removal of vertebral bone from both the upper and lower vertebrae.

63. The surgical method of claim 60 wherein the vertebral bone is facet material.

64. The surgical method of claim 59 further comprising rotating the cutting tool to remove the vertebral tissue extending into the interior of the distal portion.

65. The surgical method of claim 64 wherein the rotating of the cutting tool involves trephining.

66. The surgical method of claim 64 wherein the rotating uses the uninterrupted side wall of the proximal portion of the guide sleeve to receive and guide the cutting tool through the guide sleeve generally along the longitudinal axis.

67. The surgical method of claim 59 wherein the side wall of the distal portion has an inner diameter, the cutting tool including a cutting head having an outer diameter substantially equal to the inner diameter.

68. The surgical method of claim 67 wherein the spinal implant has an outer diameter substantially equal to the inner diameter.

69. The surgical method of claim 59 wherein said opening is positioned generally opposite the dural region of the spine.

70. The surgical method of claim 59 further comprising:

providing a spinal distractor;

inserting the distractor into the disc space to spread apart the upper and lower vertebra to a predetermined spacing;

placing the guide sleeve over the distractor with the opening positioned generally opposite the dural region of the spine; and extracting the distractor from the disc space prior to inserting the cutting tool.

* * * * *